(12) United States Patent (10) Patent No.: US 9,247,942 B2
Rudakov et al. (45) Date of Patent: Feb. 2, 2016

(54) REVERSIBLE TUBAL CONTRACEPTIVE DEVICE

(75) Inventors: Leon Rudakov, San Marcos, CA (US); Tanner J. Hargens, Charlotte, NC (US); Phillip M. Leopold, North Barrington, IL (US)

(73) Assignee: ArtVentive Medical Group, Inc., Carlsbad, CA (US)

( * ) Notice: Subject to any disclaimer, the term of this patent is extended or adjusted under 35 U.S.C. 154(b) by 167 days.

(21) Appl. No.: 13/367,338

(22) Filed: Feb. 6, 2012

(65) Prior Publication Data

US 2012/0192872 A1 Aug. 2, 2012

Related U.S. Application Data

(63) Continuation-in-part of application No. 12/826,593, filed on Jun. 29, 2010.

(51) Int. Cl.
*A61B 17/12* (2006.01)
*A61F 6/14* (2006.01)
(Continued)

(52) U.S. Cl.
CPC ....... *A61B 17/12036* (2013.01); *A61B 17/1204* (2013.01); *A61B 17/12104* (2013.01);
(Continued)

(58) Field of Classification Search
CPC .............. A61F 2/02; A61F 2/01; A61F 2/013; A61F 2/004; A61F 2/90; A61F 2/86; A61F 2/07; A61F 2/92; A61F 2/88; A61F 2002/018; A61F 2002/016; A61F 2002/011; A61F 2002/823; A61F 2002/075; A61F 2002/9528; A61F 2002/9505; A61F 2002/9511; A61F 2002/9534; A61F 2002/821; A61F 2230/0067; A61F 2230/008; A61F 5/0089; A61F 5/0079

USPC .......... 623/23.72, 1.15, 1.16, 1.3, 1.31, 1.13, 623/1.18, 1.12, 23.66, 23.7, 23.69, 1.11, 623/1.24, 1.23; 606/108, 192, 194, 198, 606/191, 157, 158, 200, 213, 151, 193; 604/8; 128/832, 830, 838, 841; 600/37, 600/29–32

See application file for complete search history.

(56) References Cited

U.S. PATENT DOCUMENTS 3,805,767 A 4/1974 Erb
3,868,956 A 3/1975 Alfidi et al.
(Continued)

FOREIGN PATENT DOCUMENTS

CN 2527227 Y 12/2002
EP 1188413 3/2002
(Continued)

OTHER PUBLICATIONS

Aydogan, Transcatheter Embolization Treatment of Coronary Arteriovenous Fistulas, Asian Cardiovascular & Thoracic Annals, 2003, pp. 63-67, vol. 11, No. 1.
(Continued)

*Primary Examiner* — Jocelin Tanner
(74) *Attorney, Agent, or Firm* — Nathan S. Smith; McDermott Will & Emery LLP

(57) ABSTRACT

Described are apparatus and methods for preventing sperm passage through a reproductive structure of a patient, and also for subsequently reversing the preventative measure in order to restore fertility to the patient. In some embodiments, the apparatus includes an elongate member arranged to form a frame having a distal and proximal opening and configured to be positioned within a lumen of the reproductive structure. The apparatus may also have a flow reducing member coupled to the frame such that when the frame is positioned within the lumen, the flow reducing member substantially impedes, reduces, or totally obstructs passage of sperm through the lumen.

23 Claims, 22 Drawing Sheets

(51) Int. Cl.
  *A61F 6/18* (2006.01)
  *A61F 6/20* (2006.01)
  *A61F 6/22* (2006.01)
  *A61B 17/00* (2006.01)

(52) U.S. Cl.
  CPC ..... *A61B17/12109* (2013.01); *A61B 17/12145* (2013.01); *A61F 6/146* (2013.01); *A61F 6/18* (2013.01); *A61F 6/20* (2013.01); *A61F 6/225* (2013.01); *A61B 17/12113* (2013.01); *A61B 2017/00809* (2013.01); *A61B 2017/1205* (2013.01); *A61B 2017/1209* (2013.01); *A61B 2017/12054* (2013.01)

(56) References Cited

U.S. PATENT DOCUMENTS

| | | |
|---|---|---|
| 3,918,431 A | 11/1975 | Sinnreich |
| 4,013,063 A | 3/1977 | Bucalo |
| 4,245,623 A | 1/1981 | Erb |
| 4,553,545 A | 11/1985 | Maass et al. |
| 4,649,922 A | 3/1987 | Wiktor |
| 4,682,592 A | 7/1987 | Thorsgard |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A | 12/1995 | Limon |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,607,445 A | 3/1997 | Summers |
| 5,674,287 A | 10/1997 | Slepian et al. |
| 5,693,083 A | 12/1997 | Baker et al. |
| 5,725,552 A | 3/1998 | Kotula et al. |
| 5,733,329 A | 3/1998 | Wallace et al. |
| 5,772,668 A | 6/1998 | Summers et al. |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,868,782 A | 2/1999 | Frantzen |
| 5,902,266 A | 5/1999 | Leone et al. |
| 5,922,009 A | 7/1999 | Epstein et al. |
| 5,925,074 A | 7/1999 | Gingras et al. |
| 5,928,260 A | 7/1999 | Chin et al. |
| 5,944,738 A | 8/1999 | Amplatz et al. |
| 5,957,929 A | 9/1999 | Brenneman |
| 5,979,446 A | 11/1999 | Loy |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,506,204 B2 | 1/2003 | Mazzocchi |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |
| 6,974,473 B2 | 12/2005 | Barclay et al. |
| 6,984,244 B2 | 1/2006 | Perez et al. |
| 7,001,409 B2 | 2/2006 | Amplatz |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |

(56) References Cited

U.S. PATENT DOCUMENTS

| | | |
|---|---|---|
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0177855 A1 | 11/2002 | Greene et al. |
| 2002/0198588 A1 | 12/2002 | Armstrong et al. |
| 2003/0114922 A1* | 6/2003 | Iwasaka et al. .............. 623/1.16 |
| 2003/0125798 A1 | 7/2003 | Martin |
| 2003/0153972 A1* | 8/2003 | Helmus ........................ 623/1.15 |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1* | 7/2005 | Thinnes et al. .............. 606/200 |
| 2005/0192616 A1* | 9/2005 | Callister et al. .............. 606/193 |
| 2005/0209675 A1 | 9/2005 | Ton et al. |
| 2005/0288684 A1 | 12/2005 | Aronson et al. |
| 2006/0052822 A1 | 3/2006 | Mirizzi et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0269719 A1 | 10/2008 | Balgobin et al. |
| 2008/0302368 A1* | 12/2008 | McGuckin et al. ............ 128/831 |
| 2009/0005847 A1 | 1/2009 | Adams |
| 2009/0018562 A1 | 1/2009 | Amplatz et al. |
| 2009/0018636 A1* | 1/2009 | Gailloud et al. .............. 623/1.11 |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1 | 3/2009 | Amplatz et al. |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |

(56) References Cited

U.S. PATENT DOCUMENTS

| | | |
|---|---|---|
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0083822 A1 | 4/2012 | Anukhin et al. |
| 2012/0089216 A1 | 4/2012 | Rapaport et al. |
| 2012/0095489 A1 | 4/2012 | Rudakov et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0209310 A1 | 8/2012 | Chen et al. |
| 2012/0239077 A1 | 9/2012 | Zaver et al. |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0128780 A1 | 5/2014 | Kennedy et al. |
| 2014/0215792 A1 | 8/2014 | Leopold et al. |
| 2014/0222059 A1 | 8/2014 | Leopold et al. |

FOREIGN PATENT DOCUMENTS

| | | |
|---|---|---|
| EP | 1317908 A2 | 6/2003 |
| EP | 1600110 | 11/2005 |
| EP | 1707233 A2 | 10/2006 |
| EP | 1752112 | 2/2007 |
| EP | 1813196 | 8/2007 |
| EP | 1820436 A2 | 8/2007 |
| EP | 1852073 | 11/2007 |
| EP | 2248471 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 A | 2/2005 |
| GB | 2494820 A | 3/2013 |
| JP | H 07-000405 | 1/1995 |
| JP | 07-18501 | 7/1995 |
| JP | 2006-181015 A | 7/2006 |
| JP | 2010-532180 A | 10/2010 |
| JP | 2012-525859 A | 10/2012 |
| WO | WO-83/00997 | 3/1983 |
| WO | WO-92/14408 | 9/1992 |
| WO | WO-94/00179 A1 | 1/1994 |
| WO | WO-95/24158 | 9/1995 |
| WO | WO-95/25480 A1 | 9/1995 |
| WO | WO-95/32018 | 11/1995 |
| WO | WO-96/18361 | 6/1996 |
| WO | WO-97/13463 | 4/1997 |
| WO | WO-97/13471 | 4/1997 |
| WO | WO-97/27893 | 8/1997 |
| WO | WO-97/27897 | 8/1997 |
| WO | WO-97/27898 | 8/1997 |
| WO | WO-97/31672 | 9/1997 |
| WO | WO-98/08456 | 3/1998 |
| WO | WO-98/31308 | 7/1998 |
| WO | WO-98/31308 A1 | 7/1998 |
| WO | WO-98/34546 | 8/1998 |
| WO | WO-98/46115 A2 | 10/1998 |
| WO | WO-98/46119 | 10/1998 |
| WO | WO-99/12484 | 3/1999 |
| WO | WO-99/23976 | 5/1999 |
| WO | WO-99/25273 | 5/1999 |
| WO | WO-99/44542 A2 | 9/1999 |
| WO | WO-99/48545 | 9/1999 |
| WO | WO-99/49793 | 10/1999 |
| WO | WO-99/49910 A2 | 10/1999 |
| WO | WO-99/62430 | 12/1999 |
| WO | WO-00/09195 | 2/2000 |
| WO | WO-00/16847 | 3/2000 |
| WO | WO-00/27303 A2 | 5/2000 |
| WO | WO-00/67671 | 11/2000 |
| WO | WO-01/32254 | 5/2001 |
| WO | WO-01/64112 A1 | 9/2001 |
| WO | WO-01/80776 | 11/2001 |
| WO | WO-01/80777 A2 | 11/2001 |
| WO | WO-01/89413 A2 | 11/2001 |
| WO | WO-02/03889 | 1/2002 |
| WO | WO-03/001970 A2 | 1/2003 |
| WO | WO-03/073961 | 9/2003 |
| WO | WO-03/073962 | 9/2003 |
| WO | WO-03/101518 | 12/2003 |
| WO | WO-2004/006804 | 1/2004 |
| WO | WO-2004/073557 A2 | 9/2004 |
| WO | WO-2005/020786 A2 | 3/2005 |
| WO | WO-2005/092241 | 10/2005 |
| WO | WO-2005/117755 A2 | 12/2005 |
| WO | WO-2006/017470 A2 | 2/2006 |
| WO | WO-2006/028943 | 3/2006 |
| WO | WO-2006/031602 | 3/2006 |
| WO | WO-2006/034153 A2 | 3/2006 |
| WO | WO-2006/074163 A2 | 7/2006 |
| WO | WO-2006/096342 | 9/2006 |
| WO | WO-2006/111801 A2 | 10/2006 |
| WO | WO-2006/134354 | 12/2006 |
| WO | WO-2007/061927 A2 | 5/2007 |
| WO | WO-2007/070544 A2 | 6/2007 |
| WO | WO-2007/085373 | 8/2007 |

(56) References Cited

FOREIGN PATENT DOCUMENTS

| | | |
|---|---|---|
| WO | WO-2007/127351 | 11/2007 |
| WO | WO-2007/149844 A2 | 12/2007 |
| WO | WO-2008/010197 A2 | 1/2008 |
| WO | WO-2008/100790 A2 | 8/2008 |
| WO | WO-2008/112501 A2 | 9/2008 |
| WO | WO-2008/153653 | 12/2008 |
| WO | WO-2009/064618 | 5/2009 |
| WO | WO-2009/077845 A2 | 6/2009 |
| WO | WO-2009/088905 | 7/2009 |
| WO | WO-2009/124288 | 10/2009 |
| WO | WO-2009/126747 | 10/2009 |
| WO | WO-2010/009019 | 1/2010 |
| WO | WO-2010/047644 | 4/2010 |
| WO | WO-2010/047644 A1 | 4/2010 |
| WO | WO-2010/075565 A2 | 7/2010 |
| WO | WO-2010/085344 A1 | 7/2010 |
| WO | WO-2010/096717 | 8/2010 |
| WO | WO-2010/130617 | 11/2010 |
| WO | WO-2010/135352 A1 | 11/2010 |
| WO | WO-2010/146581 | 12/2010 |
| WO | WO-2010/148246 A2 | 12/2010 |
| WO | WO-2011/011581 A2 | 1/2011 |
| WO | WO-2011/153304 | 12/2011 |
| WO | WO-2011/163157 A2 | 12/2011 |
| WO | WO-2012/002944 | 1/2012 |
| WO | WO-2012/040380 | 3/2012 |
| WO | WO-2012/067724 | 5/2012 |
| WO | WO-2012/109367 | 8/2012 |
| WO | WO-2012/111137 | 8/2012 |
| WO | WO-2012/120490 A2 | 9/2012 |
| WO | WO-2012/131672 A2 | 10/2012 |
| WO | WO-2012/134761 | 10/2012 |
| WO | WO-2012/135859 A2 | 10/2012 |
| WO | WO-2012/166804 | 12/2012 |
| WO | WO-2013/055703 A1 | 4/2013 |
| WO | WO-2013/059511 A1 | 4/2013 |
| WO | WO-2013/067299 | 5/2013 |

OTHER PUBLICATIONS

Berguer et al., Cure by Combination of Operation and Detachable Intravascular Balloon, Ann. Surg. Jul. 1982, pp. 65-68, vol. 196, No. 1.
Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.
DeSouza et al., Embolization with Detachable Balloons—Applications Outside the Head, Clinical Radiology, Apr. 21, 1992, pp. 170-175, vol. 46.
Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.
Hawkins et al., The Permeability of Detachable Latex Rubber Balloons—An In Vitro Study, Investigative Radiology, Dec. 1987, pp. 969-972, vol. 22.
Hirai et al., Emergency Balloon Embolization for Carotid Artery Rupture Secondary to Postoperative Infection, Cardiovasc Intervent Radiol, 1996, pp. 50-52, vol. 19.
Kadir et al., Therapeutic Embolization of the Kidney with Detachable Silicone Balloons, The Journal of Urology, Jan. 1983, pp. 11-13, vol. 129.
Kallmes et al., The Use of Hydrocoil for Parent Artery Occlusion, AJNR Am J Neuroradiol, Sep. 2004, pp. 1409-1410, vol. 25.
Kaufman, et al., Detachable Balloon-Modified Reducing Stent to Treat Hepatic Insufficiency After Transjugular Intrahepatic Portosystemic Shunt Creation, J Vasc Interv Radiol., May 2003, pp. 635-638, vol. 14, No. 5.
Luo, Chao-Bao et al., Endovascular Treatment of the Carotid Artery Rupture with Massive Hemorrhage, J. Chin Med Assoc., Mar. 2003.
Makita, et al., Guide-Wire-Directed Detachable Balloon: Clinical Application in Treatment of Varicoceles, Radiology, 1992, pp. 575-577, vol. 183.
Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.
Pollak et al., Clinical Results of Transvenous Systemic Embolotherapy with a Neuroradiologic Detachable Balloon, Radiology, May 1994, pp. 477-482, vol. 191, No. 2.
Reidy et al., Transcatherer Occlusion of Coronary to Bronchial Anastomosis by Detachable Balloon Combined with Coronary Angioplasty at Same Procedure, Brit Heart J. 1983, pp. 284-287, vol. 49.
Reidy et al., Transcatheter Occlusion of a Blalock-Taussig Shunt with a Detachable Balloon in a Child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic Arterioportal Fistula and its Treatment with Detachable Balloon and Transcatheter Embolization with Coils and Microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.
Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.
Marshall et al., Treatment of Traumatic Renal Arteriovenous Fistulas by Detachable Silicone Balloon Embolization, The Journal of Urology, Aug. 1979, pp. 237-239, vol. 122.
U.S. Appl. No. 13/828,974, filed Mar. 14, 2013.
U.S. Appl. No. 14/044,794, filed Oct. 2, 2013.
U.S. Appl. No. 14/101,171, filed Dec. 9, 2013.
U.S. Appl. No. 14/281,797, filed May 19, 2014.

* cited by examiner

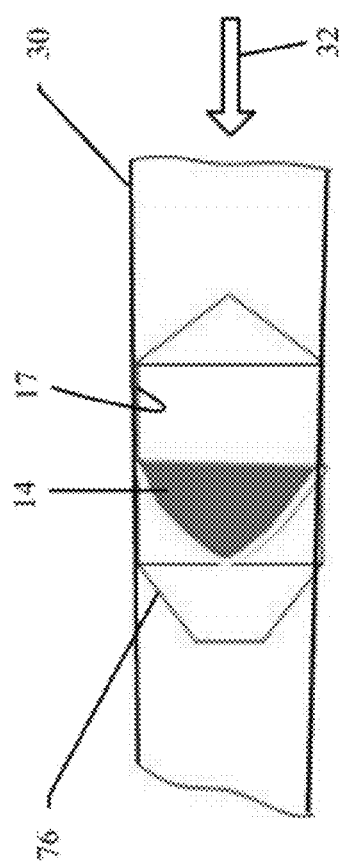
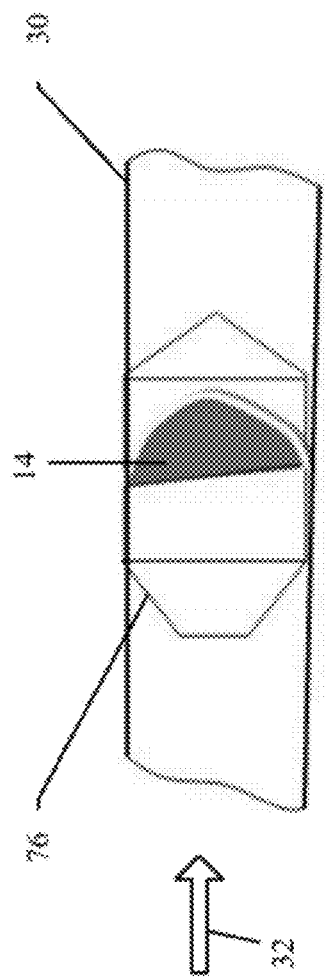
FIG. 5A
FIG. 5B

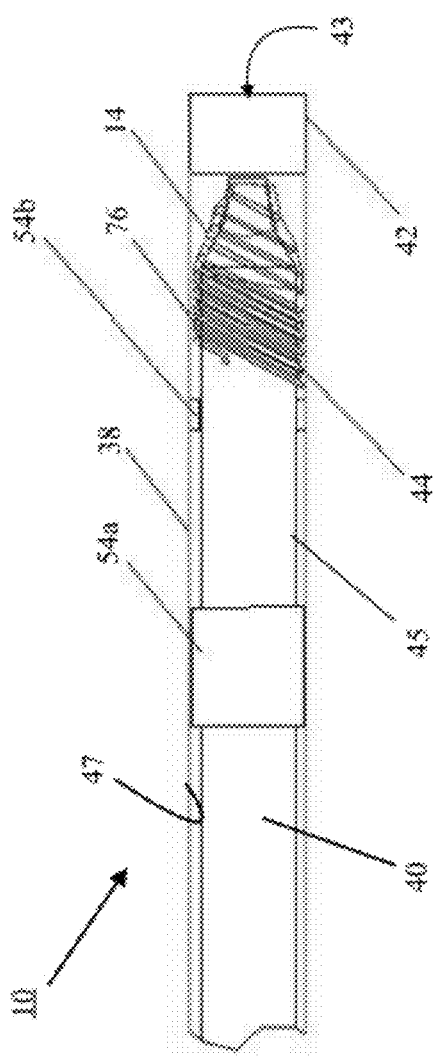
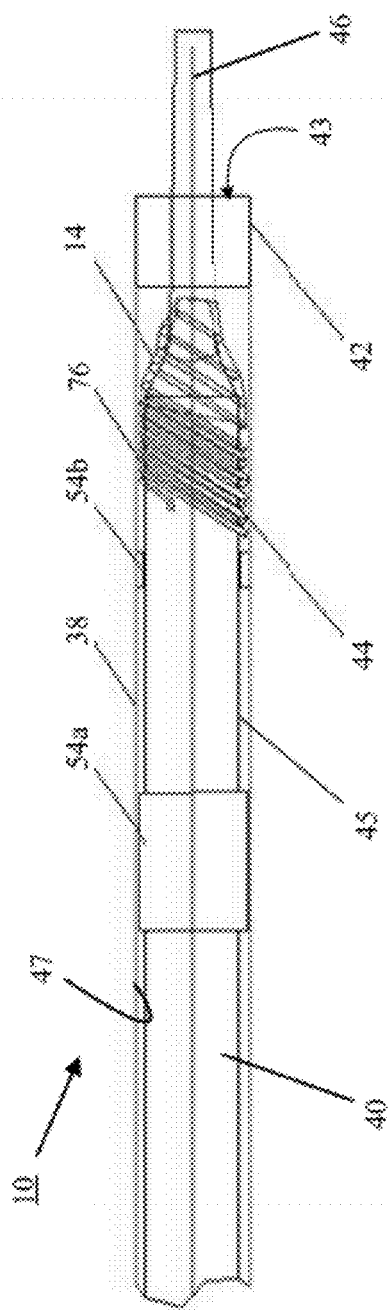
FIG. 7A
FIG. 7B

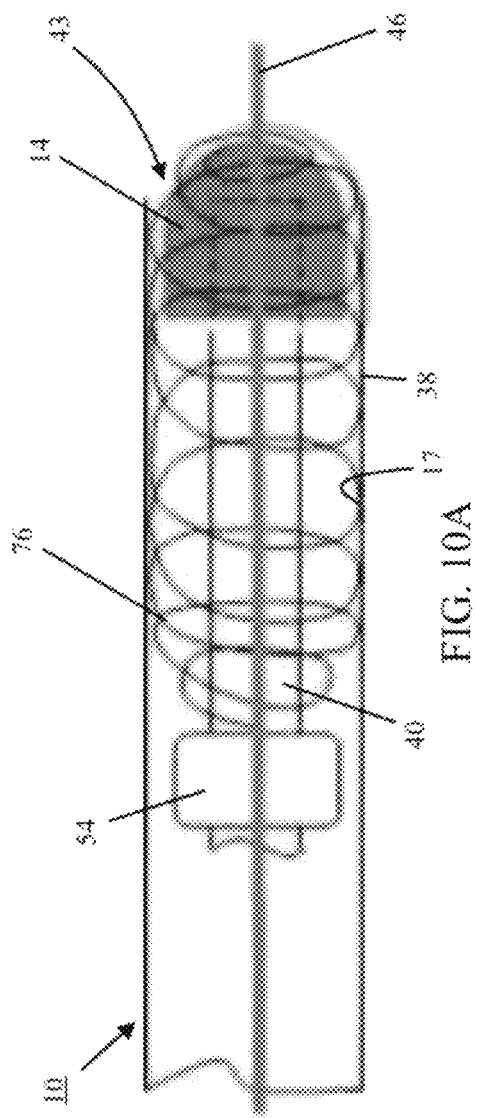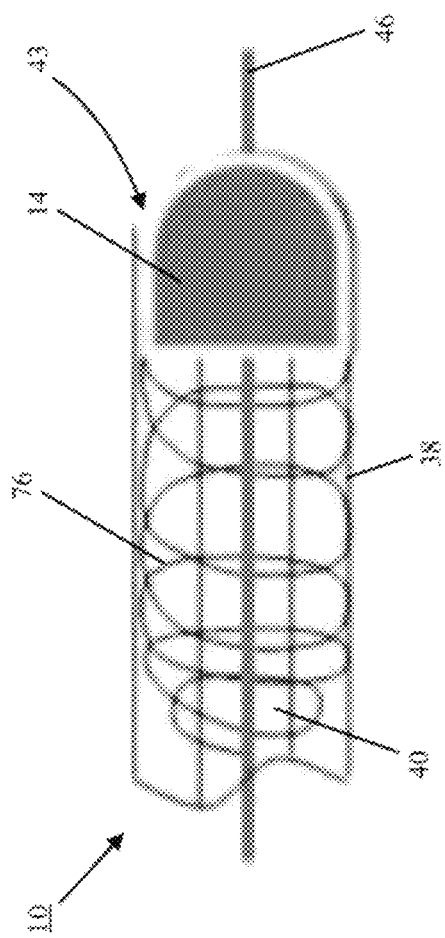
FIG. 10A
FIG. 10B

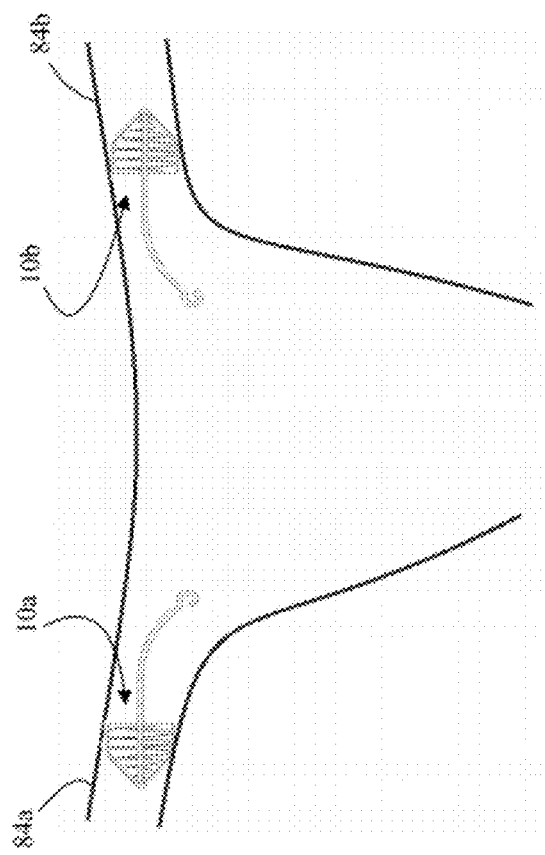
FIG. 20
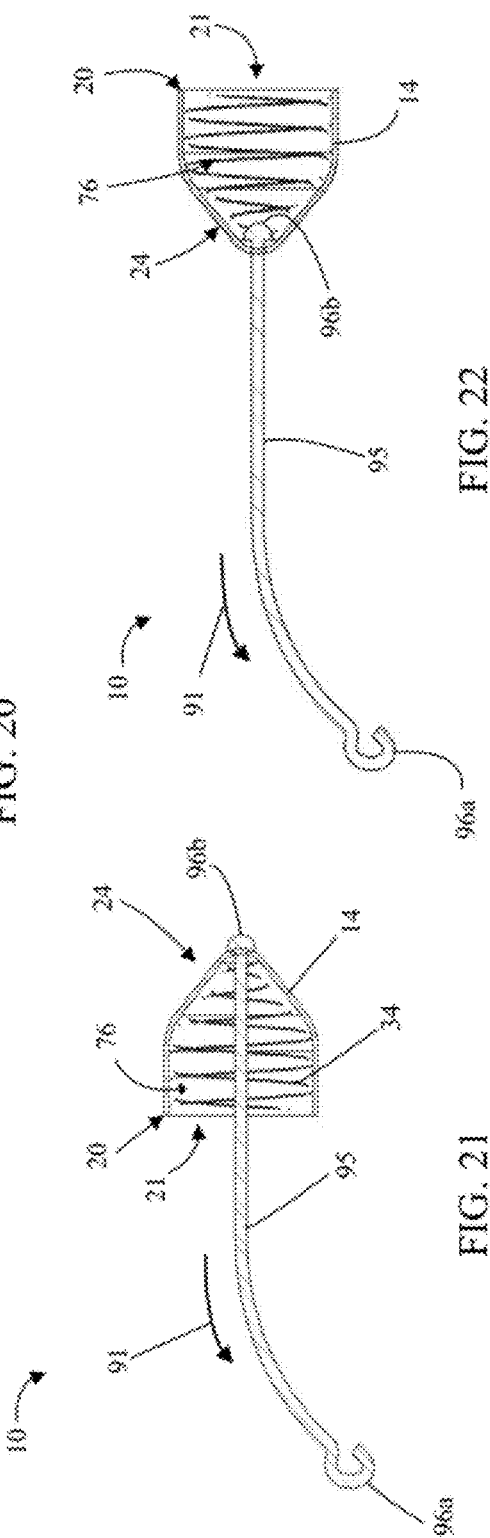
FIG. 22
FIG. 21

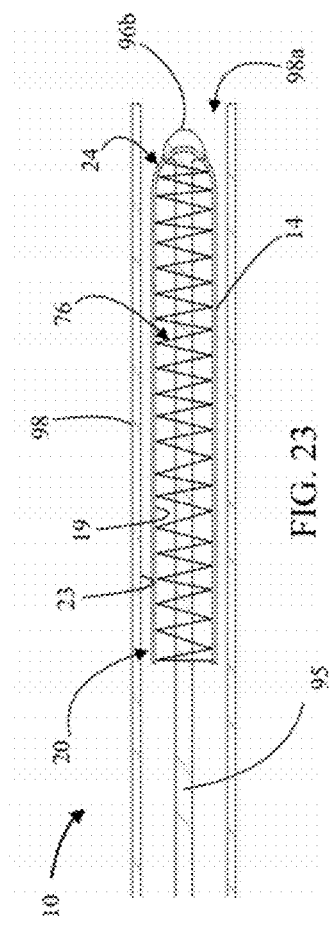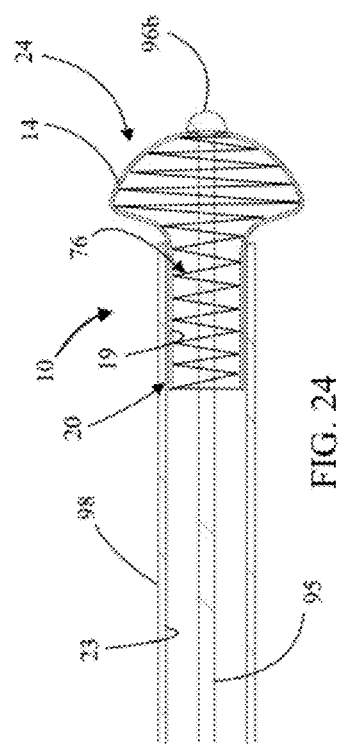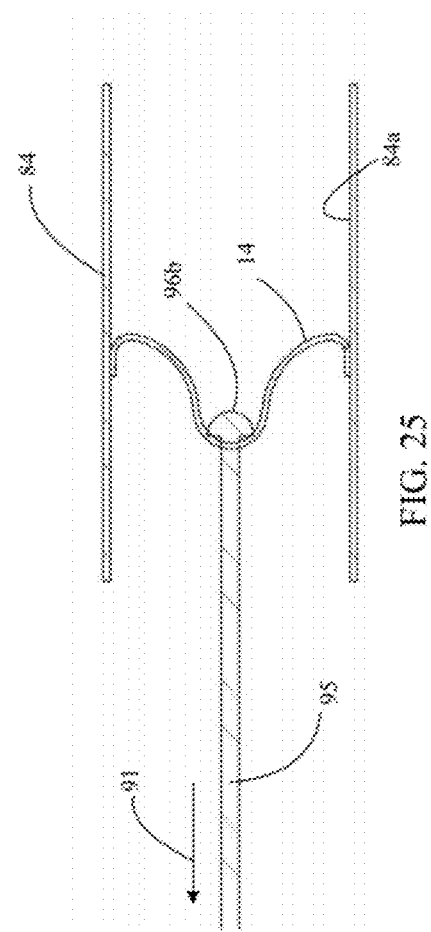

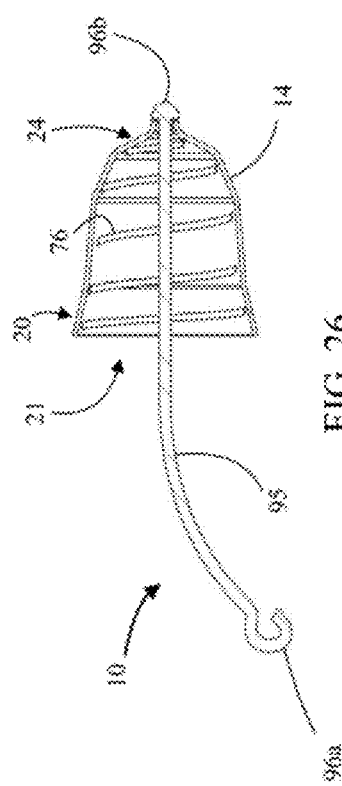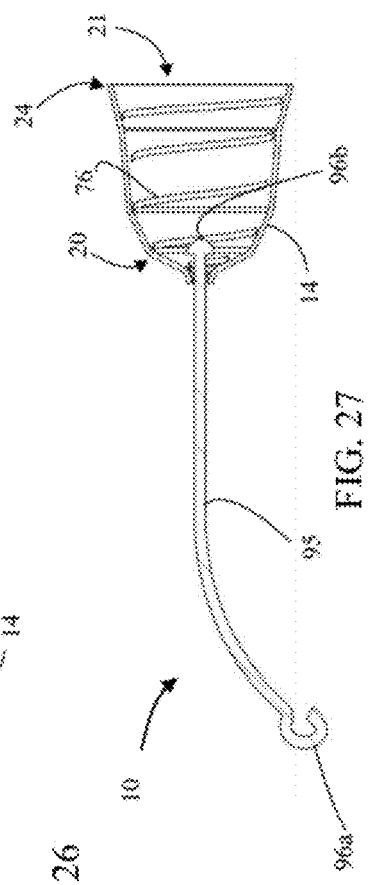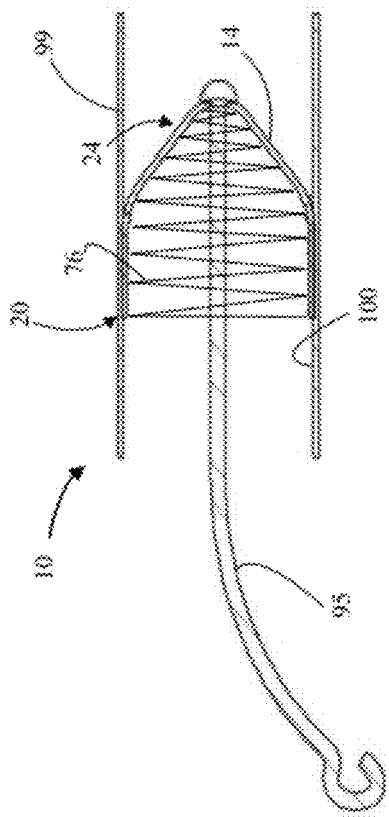

REVERSIBLE TUBAL CONTRACEPTIVE DEVICE

RELATED APPLICATIONS

The present application claims priority to and is a continuation-in-part of co-pending U.S. patent application Ser. No. 12/826,593, entitled "Reducing Flow Through a Tubular Structure," filed on Jun. 29, 2010, the contents of which are hereby incorporated by reference in their entirety for all purposes.

FIELD

The present invention generally relates to methods and apparatus for reducing or stopping flow through a tubular structure of a patient. More particularly, the present invention relates to methods and apparatus for preventing passage of sperm through a reproductive structure of a patient, and subsequently reversing the preventative measure in order to restore fertility to the patient.

BACKGROUND

Devices exist for stenting tubular structures in patients. Stents typically maintain patency in tubular structures such as blood vessels. As a result, flow of fluid such as blood through the tubular structures is generally maintained. Two occlusion devices on the market, ESSURE® and ADIANA®, are used to permanently block the fallopian tubes. These irreversible contraception devices rely on scar tissue growth around the device to occlude the fallopian tube.

SUMMARY

Problems associated with typical devices for occluding flow through tubular structures of patients include inaccurate deployment and positioning of these devices within the tubular structures, as well as having continuous and significant residual flow. These devices, once deployed, do not provide mechanisms allowing for their repositioning and/or removal in a simple manner. Thus, once these devices have been deployed, the devices are typically committed to their initially-deployed position. It is therefore desirable to provide devices that can be used to reduce or stop flow through a tubular structure of a patient, and also allow for their repositioning and/or removal.

According to various embodiments of the subject technology, an apparatus is provided for reducing or stopping flow through a tubular structure of a patient. The apparatus comprises a first elongate member arranged to form a first frame having a distal opening and a proximal opening. The first frame is configured to be positioned within a lumen of the tubular structure. The first frame includes a proximal portion, a distal portion, and a middle portion therebetween. The distal portion is tapered such that a cross-sectional dimension of the distal opening is less than a cross-sectional dimension of the middle portion. The first frame is configured to be inverted such that the distal portion moves within and toward the middle portion for removing the first frame from within the lumen. The apparatus also comprises a first flow reducing member coupled to the first frame such that when the first frame is positioned within the lumen, the first flow reducing member substantially reduces or totally obstructs flow of at least one of emboli and fluid flowing through the lumen.

In some embodiments the first elongate member is arranged in a spiral configuration to form the first frame. In some embodiments, the first flow reducing member totally obstructs flow of the at least one of emboli and fluid flowing through the lumen. In some embodiments, the first flow reducing member is coupled to the first frame using surgical suture. In some embodiments, the first frame is further configured to expand from an undeployed configuration to a deployed configuration such that the first frame engages an inner surface of the lumen. The first frame may be expanded with a balloon or may be self expandable.

According to certain embodiments, the proximal portion is tapered such that a cross-sectional dimension of the proximal opening is less than the outer cross-sectional dimension of the middle portion. In some embodiments, the outer cross-sectional dimension of the proximal opening is larger than a cross-sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, ε-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross-section. A length of the rectangular cross-section may be between about 0.008 inches and about 0.014 inches and a width of the rectangular cross-section may be between about 0.004 inches and about 0.006 inches. Corners of the rectangular cross-section may be radiused or curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire therethrough. In some embodiments, the first flow reducing member comprises a plurality of pores each having a diameter of between about 5 microns and about 10 microns.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. The flap is configured to substantially prevent distal flow through the distal opening and facilitate proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. A cross-sectional dimension of the first coil may be less than a cross-sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood vessel, a Fallopian tube, a cervical canal, a vagina, a cervix, a vas deferens, a bronchus, a ureter, a colon, a rectum, an anus, a bile duct, and a pancreatic duct. In some embodiments, the apparatus comprises a retrieving member configured to couple to the distal portion and to retrieve the distal portion toward an interior of the first frame for inverting the first frame. The retrieving member may comprise at least one jaw having a compressed configuration and a deployed configuration. The at least one jaw may be configured to expand from the compressed configuration to the deployed configuration for coupling to the distal portion. The at least one jaw may comprise a curved portion.

In certain embodiments, the apparatus comprises a tube configured to extend through the distal opening to be positioned at a target site of the patient. The apparatus also comprises a vacuum source configured to apply a vacuum through the tube for removing at least one of emboli and fluid from the target site.

In some embodiments, the apparatus comprises an outer catheter configured to be positioned within the lumen at a first deployment site. The apparatus also comprises an inner catheter disposed within the outer catheter. The first frame is configured to be positioned between the inner catheter and the outer catheter for stowage of the first frame before the first frame is deployed within the lumen.

In some embodiments, the apparatus also comprises one or more threads formed in or on an outer surface of the inner catheter such that the first elongate member wraps around the one or more threads for securing the first elongate member to the inner catheter. In some embodiments, the apparatus comprises one or more blocks disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. The distal portion and the first flow reducing member extend distally beyond a distal opening of the outer catheter such that when the outer catheter is moved within the lumen to the first deployment site, the distally extended portion of the first flow reducing member is configured to engage a wall of the lumen to reduce friction.

In some embodiments, the apparatus comprises a first stop disposed between the outer catheter and the inner catheter. The first stop is coupled to an inner surface of the outer catheter and is disposed proximal the first frame when the first frame is positioned between the inner catheter and the outer catheter. The apparatus also comprises a second stop disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, the apparatus comprises a stop disposed between the outer catheter and the inner catheter. The stop is further disposed proximal the first frame when the first frame is positioned between the inner catheter and the outer catheter. The stop is configured to substantially prevent the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, the apparatus also comprises a guide wire configured to extend through the inner catheter and the distal opening of the first frame. In some embodiments, the apparatus also comprises a second elongate member arranged in a spiral configuration to form a second frame having a distal opening and a proximal opening. The second frame is configured to be positioned within the lumen. The second frame includes a proximal portion, a distal portion, and a middle portion therebetween. The distal portion of the second frame is tapered such that a cross-sectional dimension of the distal opening of the second frame is less than a cross-sectional dimension of the middle portion of the second frame. The second frame is configured to be inverted such that the distal portion of the second frame moves within and toward the middle portion of the second frame for removing the second frame from within the lumen. The apparatus also comprises a second flow reducing member coupled to the second frame such that when the second frame is positioned within the lumen, the second flow reducing member substantially reduces or totally obstructs flow of at least one of emboli and fluid flowing through the lumen.

In some embodiments, the second frame is configured to be positioned between the outer catheter and the guide wire for stowage of the second frame before the second frame is deployed within the lumen. The apparatus also comprises one or more threads formed in or on an outer surface of the guide wire such that the second elongate member wraps around the one or more threads for securing the second elongate member to the guide wire. In some embodiments, the apparatus comprises one or more blocks disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

According to certain embodiments, the guide wire is configured to shift distally relative to the outer catheter until the second frame extends beyond a distal opening of the outer catheter into the first deployment site for deploying the second frame from the outer catheter. The outer catheter is configured to be positioned within the lumen at a second deployment site for deploying the first frame at the second deployment site. The inner catheter is configured to shift distally relative to the outer catheter until the first frame extends beyond the distal opening of the outer catheter into the second deployment site.

In some embodiments, the guide wire is configured to shift distally relative to the outer catheter until a portion of the second frame extends beyond a distal opening of the outer catheter into the first deployment site for partially deploying the second frame from the outer catheter. The guide wire is configured to shift proximally relative to the outer catheter until the portion of the second frame is retracted proximally into the outer catheter for retracting the second frame into the outer catheter. The outer catheter is configured to be positioned within the lumen at a second deployment site for deploying the second frame at the second deployment site. The guide wire is configured to shift distally relative to the outer catheter until the second frame extends beyond the distal opening of the outer catheter into the second deployment site.

In some embodiments, the inner catheter is configured to shift distally relative to the outer catheter until the first frame extends beyond a distal opening of the outer catheter into the first deployment site for deploying the first frame from the outer catheter. In some embodiments, the inner catheter is configured to shift distally relative to the outer catheter until a portion of the first frame extends beyond a distal opening of the outer catheter into the first deployment site for partially deploying the first frame from the outer catheter. The inner catheter is configured to shift proximally relative to the outer catheter until the portion of the first frame is retracted proximally into the outer catheter for retracting the first frame into the outer catheter. The outer catheter is configured to be positioned within the lumen at a second deployment site for deploying the first frame at the second deployment site. The inner catheter is configured to shift distally relative to the outer catheter until the first frame extends beyond the distal opening of the outer catheter into the second deployment site for deploying the first frame from the outer catheter.

In some embodiments, the inner catheter comprises a proximal handle. The first frame and the first flow reducing member are deployed from the outer catheter by shifting the proximal handle and the inner catheter distally relative to the outer catheter until the first frame and the first flow reducing member extend beyond a distal opening of the outer catheter into the lumen. In some embodiments, the apparatus comprises a security block coupled to the proximal handle. The security block is configured to substantially prevent the proximal handle and the inner catheter from shifting distally relative to the outer catheter.

According to various embodiments of the subject technology, a method for reducing or stopping flow through a tubular structure of a patient is provided. The method comprises positioning a first elongate member within a lumen of the tubular structure. The first elongate member is arranged to form a first frame having a distal opening and a proximal opening. The first frame includes a proximal portion, a distal portion, and a middle portion therebetween. The distal portion is tapered such that a cross-sectional dimension of the distal opening is less than a cross-sectional dimension of the middle portion. The method also comprises substantially reducing or totally obstructing, with a first flow reducing member coupled to the first frame, flow of at least one of emboli and fluid flowing through the lumen. The method also comprises removing the first frame from within the lumen by inverting the first frame such that the distal portion moves within and toward the middle portion.

In some embodiments the first elongate member is arranged in a spiral configuration to form the first frame. In some embodiments, the method comprises totally obstructing, with the first flow reducing member coupled to the first frame, flow of the at least one of emboli and fluid flowing through the lumen. In some embodiments, the first flow reducing member is coupled to the first frame using surgical suture. In some embodiments, the method comprises expanding the first frame from an undeployed configuration to a deployed configuration such that the first frame engages an inner surface of the lumen. The first frame may be expanded with a balloon or may be self-expandable.

According to certain embodiments, the proximal portion is tapered such that a cross-sectional dimension of the proximal opening is less than the outer cross-sectional dimension of the middle portion. In some embodiments, the outer cross-sectional dimension of the proximal opening is larger than a cross-sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, ϵ-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross-section. A length of the rectangular cross-section may be between about 0.008 inches and about 0.014 inches and a width of the rectangular cross-section may be between about 0.004 inches and about 0.006 inches. Corners of the rectangular cross-section may be radiused or curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire through therethrough. In some embodiments, the first flow reducing member comprises a plurality of pores each having a diameter of between about 5 microns and about 10 microns. In some embodiments, an average thickness of the first flow reducing member is between about 0.0005 inches and about 0.006 inches.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. In some embodiments, the substantially reducing or totally obstructing comprises: substantially preventing, with the flap, distal flow through the distal opening; and facilitating, with the flap, proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. A cross-sectional dimension of the first coil may be less than a cross-sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood vessel, a Fallopian tube, a cervical canal, a vagina, a cervix, a vas deferens, a bronchus, a ureter, a colon, a rectum, an anus, a bile duct, and a pancreatic duct. In some embodiments, the removing comprises: coupling a retrieving member to the distal portion; and retrieving, with the retrieving member, the distal portion toward an interior of the first frame for inverting the first frame. The retrieving member may comprise at least one jaw having a compressed configuration and a deployed configuration. The method may further comprise expanding the at least one jaw from the compressed configuration to the deployed configuration for coupling to the distal portion. The at least one jaw may comprise a curved portion.

In some embodiments, the method further comprises extending a tube through the distal opening to position the tube at a target site of the patient. The method also comprises applying, with a vacuum source, a vacuum through the tube for removing at least one of emboli and fluid from the target site.

In some embodiments, the method further comprises positioning an outer catheter within the lumen at a first deployment site. An inner catheter is disposed within the outer catheter. The first frame is configured to be positioned between the inner catheter and the outer catheter for stowage of the first frame before the first frame is deployed within the lumen.

In some embodiments, one or more threads are formed in or on an outer surface of the inner catheter such that the first elongate member wraps around the one or more threads for securing the first elongate member to the inner catheter. In some embodiments, one or more blocks are disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied. In some embodiments, the method further comprises applying electric signals to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. In some embodiments, the distal portion and the first flow reducing member extend distally beyond a distal opening of the outer catheter. In some embodiments, the positioning the outer catheter comprises moving the outer catheter within the lumen to the first deployment site. In some embodiments, the method further comprises engaging, with the distally extended portion of the first flow reducing member, a wall of the lumen to reduce friction.

In some embodiments, a first stop is disposed between the outer catheter and the inner catheter. The first stop is coupled to an inner surface of the outer catheter and is disposed proximal the first frame when the first frame is positioned between the inner catheter and the outer catheter. A second stop is disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, a stop is disposed between the outer catheter and the inner catheter. The stop is further disposed proximal the first frame when the first frame is positioned between the inner catheter and the outer catheter. The method comprises substantially preventing, with the stop, the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, a guide wire extends through the inner catheter and the distal opening of the first frame. In some embodiments, the method further comprises positioning a second elongate member within the lumen. The second elongate member is arranged in a spiral configuration to form a second frame having a distal opening and a proximal opening. The second frame includes a proximal portion, a distal portion, and a middle portion therebetween. The distal portion of the second frame is tapered such that a cross-sectional dimension of the distal opening of the second frame is less than a cross-sectional dimension of the middle portion of the second frame. The method also comprises substantially reducing or totally obstructing, with a second flow reducing member coupled to the second frame, flow of at least one of emboli and fluid flowing through the lumen. The method also comprises removing the second frame from within the lumen by inverting the second frame such that the distal portion of the second frame moves within and toward the middle portion of the second frame.

In some embodiments, the second frame is configured to be positioned between the outer catheter and the guide wire for stowage of the second frame before the second frame is deployed within the lumen. In some embodiments, the guide wire comprises one or more threads such that the second elongate member wraps around the one or more threads for securing the second elongate member to the guide wire. In some embodiments, one or more blocks is disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. In some embodiments, the method further comprises applying electric signals to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

In some embodiments, the method further comprises deploying the second frame from the outer catheter by shifting the guide wire distally relative to the outer catheter until the second frame extends beyond a distal opening of the outer catheter into the first deployment site. The method also comprises positioning the outer catheter within the lumen at a second deployment site for deploying the first frame at the second deployment site. The method also comprises deploying the first frame from the outer catheter by shifting the inner catheter distally relative to the outer catheter until the first frame extends beyond the distal opening of the outer catheter into the second deployment site.

In some embodiments, the method further comprises partially deploying the second frame from the outer catheter by shifting the guide wire distally relative to the outer catheter until a portion of the second frame extends beyond a distal opening of the outer catheter into the first deployment site. The method also comprises retracting the second frame into the outer catheter by shifting the guide wire proximally relative to the outer catheter until the portion of the second frame is retracted proximally into the outer catheter. The method also comprises positioning the outer catheter within the lumen at a second deployment site for deploying the second frame at the second deployment site. The method also comprises deploying the second frame from the outer catheter by shifting the guide wire distally relative to the outer catheter until the second frame extends beyond the distal opening of the outer catheter into the second deployment site.

In some embodiments, the method further comprises deploying the first frame from the outer catheter by shifting the inner catheter distally relative to the outer catheter until the first frame extends beyond a distal opening of the outer catheter into the first deployment site. In some embodiments, the method comprises partially deploying the first frame from the outer catheter by shifting the inner catheter distally relative to the outer catheter until a portion of the first frame extends beyond a distal opening of the outer catheter into the first deployment site. The method also comprises retracting the first frame into the outer catheter by shifting the inner catheter proximally relative to the outer catheter until the portion of the first frame is retracted proximally into the outer catheter. The method also comprises positioning the outer catheter within the lumen at a second deployment site of the lumen for deploying the first frame at the second deployment site. The method also comprises deploying the first frame from the outer catheter by shifting the inner catheter distally relative to the outer catheter until the first frame extends beyond the distal opening of the outer catheter into the second deployment site.

In some embodiments, the inner catheter comprises a proximal handle. In some embodiments, the method further comprises deploying the first frame and the first flow reducing member from the outer catheter by shifting the proximal handle and the inner catheter distally relative to the outer catheter until the first frame and the first flow reducing member extend beyond a distal opening of the outer catheter into the lumen. In some embodiments, the method further comprises substantially preventing, with a security block coupled to the proximal handle, the proximal handle and the inner catheter from shifting distally relative to the outer catheter.

According to various embodiments of the subject technology, a method for reducing or stopping flow through a tubular structure of a patient is provided. The method comprises positioning an outer catheter within a lumen of the tubular structure at a first deployment site. An inner catheter is disposed within the outer catheter. A first elongate member is positioned between the inner catheter and the outer catheter. The first elongate member is arranged to form a first frame that can have, in some embodiments, a distal opening and a proximal opening. The first frame includes a proximal portion, a distal portion, and a middle portion therebetween. The distal portion is tapered such that a cross-sectional dimension of the distal opening is less than a cross-sectional dimension of the middle portion. The method also comprises partially deploying the first frame from the outer catheter by shifting the inner catheter distally relative to the outer catheter until a portion of the first frame extends beyond a distal opening of the outer catheter into the first deployment site. The method also comprises retracting the first frame into the outer catheter by shifting the inner catheter proximally relative to the outer catheter until the portion of the first frame is retracted proximally into the outer catheter. The method also comprises positioning the outer catheter within the lumen at a second deployment site for deploying the first frame at the second deployment site. The method also comprises deploying the first frame from the outer catheter by shifting the inner catheter distally relative to the outer catheter until the first frame extends beyond the distal opening of the outer catheter into the second deployment site. The method also comprises substantially reducing or totally obstructing, with a first flow reducing member coupled to the first frame, flow of at least one of emboli and fluid flowing through the lumen.

In some embodiments the first elongate member is arranged in a spiral configuration to form the first frame. In some embodiments, the method comprises totally obstructing, with the first flow reducing member coupled to the first frame, flow of the at least one of emboli and fluid flowing through the lumen. In some embodiments, the first flow reducing member is coupled to the first frame using surgical suture. In some embodiments, the method comprises expanding the first frame from an undeployed configuration to a deployed configuration such that the first frame engages an inner surface of the lumen. The first frame may be expanded with a balloon or may be self expandable.

According to certain embodiments, the proximal portion is tapered such that a cross-sectional dimension of the proximal opening is less than the outer cross-sectional dimension of the middle portion. In some embodiments, the outer cross-sectional dimension of the proximal opening is larger than a cross-sectional dimension of the distal opening.

In some embodiments, the first elongate member comprises at least one of stainless steel, nickel titanium (NiTi), cobalt chromium (CoCr), titanium, a polymer, a polyester based material, a tyrosine based polycarbonate, a polyethylene based material, and Teflon (e.g., including expanded Teflon). The first elongate member may also comprise at least one of polyethylene, polyglicolide, polylactide, ϵ-caprolactone, polycarbonate, hydroxyalkanote, para dioxinine, PLA, PGA, PLLA, PDLLA, PDO, and PCL. In some embodiments, the first elongate member comprises bioabsorbable material.

According to certain embodiments, the first elongate member comprises a substantially rectangular cross-section. A length of the rectangular cross-section may be between about 0.008 inches and about 0.014 inches and a width of the rectangular cross-section may be between about 0.004 inches and about 0.006 inches. Corners of the rectangular cross-section may be radiused or curved.

In some embodiments, the first frame is coated with biological glue. The biological glue may comprise glue from at least one of crab shells, spider webs, gecko feet, burrowing frogs, mussels, and caulobacter crescentus bacteria.

In some embodiments, the first flow reducing member comprises at least one of a polyurethane and a polyanhidrate. In some embodiments, the first flow reducing member comprises expanded polytetrafluoroethylene (ePTFE). In some embodiments, the first flow reducing member comprises bioabsorbable material. In some embodiments, the first flow reducing member comprises a self sealing material. The first flow reducing member may be configured to facilitate an extension of a guide wire through therethrough. In some embodiments, the first flow reducing member comprises a plurality of pores each having a diameter of between about 5 microns and about 10 microns. In some embodiments, an average thickness of the first flow reducing member is between about 0.0005 inches and about 0.006 inches.

According to certain embodiments, the first flow reducing member is disposed over an exterior of the first frame. The first flow reducing member may be disposed over the distal portion. A hole may be defined in the first flow reducing member. The hole may allow a guide wire to extend therethrough. The first flow reducing member may comprise a portion configured to partially, substantially, or totally block the hole when the guide wire is removed therefrom. Swelling material may be disposed in or on the portion. When fluid contacts the swelling material, the swelling material and the portion may be expanded to substantially or totally block the hole. In some aspects, the portion may comprise a pocket. In some aspects, the swelling material may be comprised of microparticles. In some aspects, the swelling material may comprise hydrogel.

In some embodiments, at least a portion of the first flow reducing member extends from the exterior of the first frame into an interior of the first frame through the distal opening to form a flap in the interior of the first frame. In some embodiments, the substantially reducing or totally obstructing comprises: substantially preventing, with the flap, distal flow through the distal opening; and facilitating, with the flap, proximal flow through the distal opening.

In some embodiments, an average thickness of the first flow reducing member is between about 0.0005 inches and about 0.006 inches. In some embodiments, an average thickness of a distal portion of the first flow reducing member is greater than an average thickness of a proximal portion of the first flow reducing member. The average thickness of the distal portion of the first flow reducing member may be between about 0.002 inches and about 0.012 inches and the average thickness of the proximal portion of the first flow reducing member may be between about 0.0005 inches and about 0.006 inches.

In some embodiments, the first flow reducing member is disposed over the distal opening. In some embodiments, the first flow reducing member is disposed over the proximal portion, the middle portion, and the distal portion.

According to certain embodiments, a radio-opaque marker is placed on a first coil of the first frame. A cross-sectional dimension of the first coil may be less than a cross-sectional dimension of a second coil of the first frame. The radio-opaque marker may surround an exterior of the first coil. The first coil may be adjacent to a second coil of the first frame. The first flow reducing member may be coupled to the second coil. The radio-opaque marker may comprise a platinum iridium alloy.

In some embodiments, the first flow reducing member is disposed in an interior of the first frame. The first flow reducing member may be coupled to the middle portion. The first flow reducing member may be coupled to a first coil of the first frame such that the first flow reducing member substantially covers an opening through the first coil. A portion of the first elongate member from a first point on the first elongate member to a second point on the first elongate member may form the first coil. The first flow reducing member may be coupled to the first elongate member from the first point on the first elongate member to the second point on the first elongate member. A thickness of the first coil of the first frame measured along an axial dimension of the first frame may be less than a thickness of a second coil of the first frame measured along the axial dimension of the first frame.

In some embodiments, the tubular structure comprises at least one of a blood vessel, a Fallopian tube, a cervical canal, a vagina, a cervix, a vas deferens, a bronchus, a ureter, a colon, a rectum, an anus, a bile duct, and a pancreatic duct. In some embodiments, the removing comprises: coupling a retrieving member to the distal portion; and retrieving, with the retrieving member, the distal portion toward an interior of the first frame for inverting the first frame. The retrieving member may comprise at least one jaw having a compressed configuration and a deployed configuration. The method may further comprise expanding the at least one jaw from the compressed configuration to the deployed configuration for coupling to the distal portion. The at least one jaw may comprise a curved portion.

In some embodiments, the method further comprises extending a tube through the distal opening to position the tube at a target site of the patient. The method also comprises applying, with a vacuum source, a vacuum through the tube for removing at least one of emboli and fluid from the target site.

In some embodiments, one or more threads are formed in or on an outer surface of the inner catheter such that the first elongate member wraps around the one or more threads for securing the first elongate member to the inner catheter. In some embodiments, one or more blocks are disposed on an outer surface of the inner catheter such that the first elongate member wraps around the one or more blocks for securing the first elongate member to the inner catheter. The one or more blocks may comprise electroactive polymer (EAP) and may be configured to swell when electric signals are applied to the one or more blocks. The first elongate member wrapped around the one or more blocks may be substantially locked to the one or more blocks when the electric signals are applied. In some embodiments, the method further comprises applying electric signals to the one or more blocks. The first elongate member wrapped around the one or more blocks may be substantially locked to the one or more blocks when the electric signals are applied.

In some embodiments, the inner catheter comprises a hole configured such that a proximal tip of the first elongate member extends through the hole from an exterior of the inner catheter into an interior of the inner catheter for securing the first frame to the inner catheter. In some embodiments, the inner catheter comprises a groove configured such that a proximal tip of the first elongate member is disposed in the groove for securing the first frame to the inner catheter.

In certain embodiments, the first flow reducing member is disposed over the distal portion. In some embodiments, the distal portion and the first flow reducing member extend distally beyond a distal opening of the outer catheter. In some embodiments, the positioning the outer catheter comprises moving the outer catheter within the lumen to the first deployment site. In some embodiments, the method further comprises engaging, with the distally extended portion of the first flow reducing member, a wall of the lumen to reduce friction.

In some embodiments, a first stop is disposed between the outer catheter and the inner catheter. The first stop is coupled to an inner surface of the outer catheter and is disposed proximal the first frame when the first frame is positioned between the inner catheter and the outer catheter. A second stop is disposed between the outer catheter and the inner catheter. The second stop is coupled to an outer surface of the inner catheter and is disposed proximal the first stop. When the inner catheter is shifted distally relative to the outer catheter for deploying the first frame, the second stop engages the first stop to substantially prevent the inner catheter from further distal shifting relative to the outer catheter. In some embodiments, the second stop comprises a groove configured such that a proximal tip of the first elongate member is disposed in the groove for securing the first frame to the inner catheter.

In some embodiments, a stop is disposed between the outer catheter and the inner catheter. The stop is further disposed proximal the first frame when the first frame is positioned between the inner catheter and the outer catheter. The method comprises substantially preventing, with the stop, the first frame from moving proximally relative to at least one of the outer catheter and the inner catheter. In some embodiments, the stop comprises a groove configured such that a proximal tip of the first elongate member is disposed in the groove for securing the first frame to the inner catheter.

In some embodiments, a guide wire extends through the inner catheter and the distal opening of the first frame. In some embodiments, the method further comprises positioning a second elongate member within the lumen. The second elongate member is arranged in a spiral configuration to form a second frame having a distal opening and a proximal opening. The second frame includes a proximal portion, a distal portion, and a middle portion therebetween. The distal portion of the second frame is tapered such that a cross-sectional dimension of the distal opening of the second frame is less than a cross-sectional dimension of the middle portion of the second frame. The method also comprises substantially reducing or totally obstructing, with a second flow reducing member coupled to the second frame, flow of at least one of emboli and fluid flowing through the lumen. The method also comprises removing the second frame from within the lumen by inverting the second frame such that the distal portion of the second frame moves within and toward the middle portion of the second frame.

In some embodiments, the second frame is configured to be positioned between the outer catheter and the guide wire for stowage of the second frame before the second frame is deployed within the lumen. In some embodiments, the guide wire comprises one or more threads such that the second elongate member wraps around the one or more threads for securing the second elongate member to the guide wire. In some embodiments, one or more blocks is disposed on an outer surface of the guide wire such that the second elongate member wraps around the one or more blocks for securing the second elongate member to the guide wire. The one or more blocks may comprise electroactive polymer (EAP) and are configured to swell when electric signals are applied to the one or more blocks. In some embodiments, the method further comprises applying electric signals to the one or more blocks. The second elongate member wrapped around the one or more blocks may be substantially locked to the one or more blocks when the electric signals are applied.

In some embodiments, the first flow reducing member is disposed over the distal portion of the first frame and the second flow reducing member is disposed over the proximal portion of the second frame. In some embodiments, the first flow reducing member is disposed over the distal portion of the first frame and the second flow reducing member is disposed over the distal portion of the second frame.

In some embodiments, the method further comprises deploying the second frame from the outer catheter by shifting the guide wire distally relative to the outer catheter until the second frame extends beyond a distal opening of the outer catheter into the first deployment site.

In some embodiments, the method further comprises partially deploying the second frame from the outer catheter by shifting the guide wire distally relative to the outer catheter until a portion of the second frame extends beyond a distal opening of the outer catheter into a third deployment site. The method also comprises retracting the second frame into the outer catheter by shifting the guide wire proximally relative to the outer catheter until the portion of the second frame is retracted proximally into the outer catheter. The method also comprises positioning the outer catheter within the lumen at a fourth deployment site for deploying the second frame at the fourth deployment site. The method also comprises deploying the second frame from the outer catheter by shifting the guide wire distally relative to the outer catheter until the second frame extends beyond the distal opening of the outer catheter into the fourth deployment site.

In some embodiments, the inner catheter comprises a proximal handle. In some embodiments, the method further comprises deploying the first frame and the first flow reducing member from the outer catheter by shifting the proximal handle and the inner catheter distally relative to the outer catheter until the first frame and the first flow reducing member extend beyond a distal opening of the outer catheter into the lumen. In some embodiments, the method further comprises substantially preventing, with a security block coupled to the proximal handle, the proximal handle and the inner catheter from shifting distally relative to the outer catheter.

In some embodiments, an apparatus for prevention of sperm passage through a reproductive structure of a patient is disclosed. The apparatus may include an elongate member forming a frame having a distal opening and a proximal opening and being configured to be positioned within a lumen of the reproductive structure, the frame further having a proximal portion, a distal portion, and a middle portion extending therebetween. The apparatus may further include a flow reducing member coupled to the frame such that when the frame is positioned within the lumen, the flow reducing member reduces or totally obstructs passage of sperm through the lumen. In some embodiments, the frame is formed by a plurality of contiguous coils axially-offset from each other. Moreover, the frame may be made of a shape-memory material expandable from a compressed configuration and into a deployed configuration upon being unrestrained. In one or more embodiments, the flow reducing member is coupled to one of the plurality of contiguous coils in an interior of the frame such that the flow reducing member substantially encompasses an opening defined by the one of the plurality of contiguous coils.

In some embodiments, the flow reducing member is disposed over an exterior of the frame. For example, the flow reducing member may be disposed over the distal portion of the frame. In at least one embodiment, the flow reducing member closes the distal opening of the frame but the proximal opening remains unobstructed. In one or more embodiments, the middle portion of the apparatus is tapered such that a cross-sectional dimension of the middle portion is less than a cross-sectional dimension of at least one of the proximal and distal portions.

In some embodiments, the apparatus may further include a withdrawal component configured to be engaged by a retrieving device to retrieve all or a portion of the apparatus. The withdrawal component may be coupled to the distal portion of the frame and the withdrawal component is configured to be pulled toward an interior of the frame to invert the frame. In other embodiments, the withdrawal component is coupled to the flow reducing member.

In some embodiments, the apparatus may also include a tubular scaffold configured to be positioned within the lumen and separate the lumen from the flow reducing member and the frame. The tubular scaffold may be made of a shape memory material expandable from a compressed configuration to a deployed configuration when unrestrained.

In some embodiments, the flow reducing member includes one or more occlusion caps. In one or more embodiments, at least one of the one or more occlusion caps is a biodegradable material. The biodegradable material may have a degradation profile that is stable until a triggering event occurs. In some embodiments, the flow reducing member is at least partially coated with a tissue growth inhibitor.

In some embodiments, a method for preventing the passage of sperm through a reproductive structure of a patient is disclosed. The method may include positioning a first elongate member within a first lumen of the reproductive structure, the first elongate member forming a first frame having a first proximal portion that defines a first proximal opening, and a first distal portion that defines a first distal opening. The method may also include expanding the first frame within the first lumen, and expanding a first flow reducing member coupled to the first frame. The method may further include reducing or totally obstructing the passage of sperm through the first lumen with the first flow reducing member.

In some embodiments, the method may further include positioning a tubular scaffold in the first lumen to separate the first lumen from the first flow reducing member and the first frame. The method may also include injecting at least one of an occlusion gel and an occlusion foam within or around the first elongate member. The method may further include substantially covering the first distal opening with the first flow reducing member. In some embodiments, the method may further include positioning a second elongate member within a second lumen of the reproductive structure, the second elongate member forming a second frame having a second proximal portion that defines a second proximal opening, and a second distal portion that defines a second distal opening, expanding the second frame within the second lumen, expanding a second flow reducing member coupled to the second frame, and reducing or totally obstructing the passage of sperm through the second lumen with the second flow reducing member.

In some embodiments, a method for restoring fertility to a patient having a contraceptive apparatus positioned within a reproductive structure of the patient is disclosed. The method may include deactivating the contraceptive apparatus, the contraceptive apparatus comprising an elongate member forming a frame having a proximal portion and a distal portion, and a flow reducing member coupled to the frame, and allowing sperm to pass through the flow reducing member. In one or more embodiments, deactivating the contraceptive apparatus includes breaching the integrity of the flow reducing member. In other embodiments, the flow reducing member is an absorbable polymer and deactivating the contraceptive apparatus includes accelerating degradation of the absorbable polymer. In yet other embodiments, the contraceptive apparatus further includes a withdrawal component coupled to the frame, and deactivating the contraceptive apparatus includes engaging the withdrawal component with a retrieving device, and pulling the withdrawal component proximally to remove all or a portion of the contraceptive device from the reproductive structure. In some embodiments, the withdrawal component is coupled to the distal portion of the frame and pulling the withdrawal component proximally includes pulling the distal portion of the frame toward an interior of the frame to invert the frame.

Additional features and advantages of the invention will be set forth in the description below, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention and are incorporated in and constitute a part of this specification, illustrate aspects of the invention and together with the description serve to explain the principles of the invention.

FIGS. 5A and 5B illustrate an apparatus deployed within a lumen of a tubular structure of a patient, in accordance with various embodiments of the subject technology.

FIGS. 7A and 7B illustrate detailed views of a frame and a flow reducing member positioned within an outer catheter, in accordance with various embodiments of the subject technology.

FIGS. 10A and 10B illustrate an example of a frame and a flow reducing member positioned within an outer catheter, in accordance with various embodiments of the subject technology.

FIG. 20 illustrates a pair of deployed contraceptive devices, in accordance with various embodiments of the subject technology.

FIG. 21 illustrates an exemplary contraceptive device in its deployed configuration, in accordance with various embodiments of the subject technology.

FIG. 22 illustrates the contraceptive device of FIG. 21 in an inverted configuration for removal, in accordance with various embodiments of the subject technology.

FIG. 23 illustrates the contraceptive device in a compressed configuration prior to deployment, in accordance with various embodiments of the subject technology.

FIG. 24 illustrates the contraceptive device of FIG. 23 in a partially-deployed configuration, in accordance with various embodiments of the subject technology.

FIG. 25 illustrates the contraceptive device of FIG. 23 as it is being removed from a tubular structure, in accordance with various embodiments of the subject technology.

FIG. 26 illustrates an alternative configuration of a contraceptive device, in accordance with various embodiments of the subject technology.

FIG. 27 illustrates another alternative configuration of the contraceptive device, in accordance with various embodiments of the subject technology.

FIG. 28 illustrates the contraceptive device as deployed within a tubular scaffold, in accordance with various embodiments of the subject technology.

DETAILED DESCRIPTION

In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail so as not to obscure the present invention.

Figure 1:
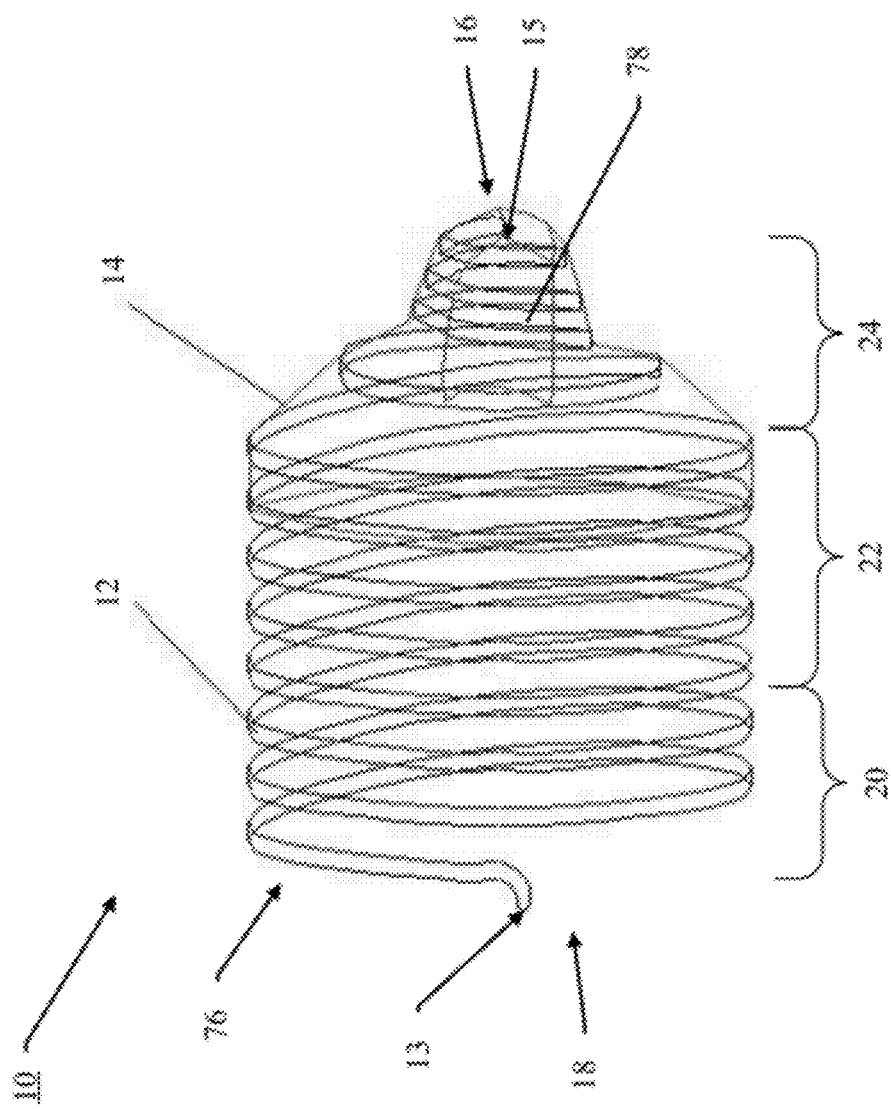
FIG. 1 illustrates an example of an apparatus for reducing or stopping flow through a tubular structure of a patient, in accordance with various embodiments of the subject technology.

FIG. 1 illustrates an example of apparatus 10 for reducing or stopping flow through a tubular structure of a patient, in accordance with various embodiments of the subject technology. The apparatus 10 comprises an elongate member 12 arranged to form a frame 76 having a distal opening 16 and a proximal opening 18. The frame 76 is configured to be positioned within a lumen of the tubular structure. The frame 76 includes a proximal portion 20, a distal portion 24, and a middle portion 22 extending therebetween. The distal portion 24 may be tapered such that a cross-sectional dimension of the distal opening 16 is less than a cross-sectional dimension of the middle portion 22. In one or more embodiments, the tapered distal portion 24 may allow for easy passage of a guide wire or a retrieval tool to pass therethrough. The frame 76 may be configured to be inverted such that the distal portion 24 moves within and toward the middle portion 22 for removing the frame 76 from within the lumen.

The apparatus 10 may also include a flow reducing member 14 coupled to the frame 76 such that when the frame 76 is positioned within the lumen, the flow reducing member 14 substantially reduces or totally obstructs flow of at least one of emboli and fluid flowing through the lumen. In one or more embodiments, the flow reducing member 14 may be secured and placed inside and/or outside of the frame 76. In some aspects, the flow reducing member 14 may be coupled to the frame 76 using surgical suture.

In some embodiments, the elongate member 12 is formed by a plurality of contiguous coils 34 (see FIG. 3) axially-offset from each other and generally arranged in a spiral configuration. As a result of the spiral configuration, the frame 76 may be configured to be expanded radially to engage an inner surface of the lumen. Should the inner surface of the lumen apply a radially compressive force on any portion of the frame 76, the spiral configuration disperses such a force along the entirety of the elongate member 12, thereby providing strong structural support for the apparatus 10 while arranged within the lumen. In some embodiments, the spiral configuration of the elongate member 12 allows the frame 76 to withstand long-term pulsatile loads of torque and bending, and reduces the risk of fatigue breaks, cracks, etc.

In some embodiments, the elongate member 12 may be defined by more or less coils than are depicted in FIG. 1. For example, the number of axially-spaced coils in the spiral configuration may vary depending on the required size and compressibility of the frame 76, a desired placement of the apparatus 10, and/or other factors known to those skilled in the art. In some embodiments, the elongate member 12 is highly flexible while providing sufficient rigidity to be guided through the lumen. In at least one embodiment, the tapered distal portion 24 is defined by or otherwise includes one or more of the coils of the frame 76.

In some embodiments, the frame 76 may be reduced in the radial direction by applying an axial force to a tip or end of the elongate member 12, thereby allowing the apparatus 10 to be disengaged from the inner surface of the lumen and repositioned and/or removed. For example, an axial force in the proximal direction may be applied to a proximal tip 13 of the elongate member 12, resulting in the radial reduction of the frame 76. Although the elongate member 12 is depicted in FIG. 1 as arranged in the spiral configuration, other suitable configurations known to those of ordinary skill in the art may be used. In some embodiments, the elongate member 12 includes one or more anchors configured to engage an inner surface of the lumen for resisting axial movement of the frame 76 when the frame 76 is deployed within the lumen. For example, the one or more anchors may be protrusions, or hair-like wires of the same material as the elongate member 12.

According to certain embodiments, the apparatus 10 may be removed from within the lumen by inverting the frame 76. For example, an axial force in the proximal direction may be applied to the distal portion 24 such that the distal portion 24 moves inverts within itself and toward the middle portion 22. In some embodiments, such an inversion causes the elongate member 12 to "unwind" from its spiral configuration, in which case the axial force may continue to be applied until the elongate member 12 disengages from the inner surface of the lumen. In some embodiments, the elongate member 12 may maintain its spiral configuration after the inversion, but otherwise exhibit a reduced cross-sectional dimension as an inverted frame 76. In such a case, the inverted frame 76 may be easily removed from within the lumen because of the reduced cross-sectional dimension.

According to various embodiments of the subject technology, the elongate member 12 may be made of at least one of stainless steel, nickel titanium (NiTi), cobalt chromium (CoCr), titanium, a polymer, a polyester based material, a tyrosine based polycarbonate, a polyethylene based material, polytetrafluoroethylene (PTFE) (i.e., TEFLON® and including expanded polytetrafluoroethylene (ePTFE)), combinations thereof, and/or the like. In some embodiments, the elongate member 12 may be made of at least one of polyethylene, polyglicolide, polylactide, ε-caprolactone, polycarbonate, hydroxyalkanote, para dioxinine, PLA, PGA, PLLA, PDLLA, PDO, PCL, combinations thereof, and/or the like. In some embodiments, the elongate member 12 and/or the flow reducing member 14, may be formed of a bioabsorbable material that allows for their respective, controlled degradation. In some embodiments, the elongate member 12 and/or the flow reducing member 14 may be formed of a bioabsorbable material configured to provide a controlled degradation of between about 3 months to about 3 years, depending on the desired application of the apparatus 10. In some embodiments, the controlled degradation may be less than about 3 months or greater than about 3 years. For example, hydrolysis of ester linkages or effects of enzymatic degradation may be utilized for the controlled degradation.

In some embodiments, the frame 76 may be coated with various suitable agents that facilitate engagement of the frame 76 to the inner surface of the lumen. For example, the frame 76 may be coated with a biological glue, such as, but not limited to, glue from at least one of crab shells, spider webs, gecko feet, burrowing frogs, mussels, caulobacter crescentus bacteria, combinations thereof, or the like. In some embodiments, the frame 76 may be coated with a friction-resistant coating, such as a friction-resistant polymer coating, configured to facilitate slidable engagement between the frame 76 and the inner surface of the lumen.

In some embodiments, radio-opaque markers may be located on the frame 76, the flow reducing member 14, and/or a catheter delivering the apparatus 10 for endovascular or other image-guided procedures. For example, a radio-opaque marker may be placed on a first coil of the frame 76. In some embodiments, a cross-sectional dimension of the first coil is less than a cross-sectional dimension of a second coil of the frame 76, which will allow space for the radio-opaque marker to surround, at least in part, an exterior of the first coil. In some embodiments, the first coil is arranged adjacent the second coil, and the flow reducing member 14 may be coupled to the second coil. In this regard, having the radio-opaque marker placed on the first coil adjacent the second coil where the flow reducing member 14 is coupled will allow a user of the apparatus 10 to identify where embolization may occur. In some embodiments, the radio-opaque marker may be a platinum iridium alloy or other suitable markers known to those skilled in the art.

According to various embodiments of the subject technology, the flow reducing member 14 may be used to partially or completely occlude the tubular structure into which the apparatus 10 is deployed. As used herein, the term "occlusion" may refer to either partial or complete occlusion. In some embodiments, at least a portion of the flow reducing member 14 extends from an exterior of the frame 76 into an interior of the frame 76 through the distal opening 16. Specifically, a flap 78 extending from the flow reducing member 14 may extend into the interior of the frame 76 through the distal opening 16. The flap 78 may be configured to substantially prevent distal fluid flow (e.g., from proximal toward distal) through the distal opening 16 and otherwise facilitate proximal fluid flow (e.g., from distal toward proximal) through the distal opening 16. For example, a guide wire (not shown) may be extended through the distal opening 16 for deploying the apparatus 10. Consequently, the flap 78 may be pressed against the guide wire and held in place, thereby maintaining the distal opening 16 in its open configuration. Upon removing the guide wire proximally, the flap 78 is released from engagement with the guide wire and may operate to close the distal opening 16 such that distal fluid flow through the distal opening 16 is substantially prevented. In some embodiments, the flap 78 may serve as a one-way valve to substantially or totally obstruct flow in one direction. For example, the flap 78 may substantially or totally obstruct distal flow while allowing proximal flow. As will be appreciated by those skilled in the art, such an arrangement may be advantageously used in partial lung obstruction to treat chronic obstructive pulmonary disease (COPD), for example.

In some embodiments, the flow reducing member 14 comprises at least one of a polyurethane, a polyanhidrate, polyethylene, fluoropolymers such as polytetrafluoroethylene (PTFE) and expanded polytetrafluoroethylene (ePTFE), bioabsorbable polymers, and other suitable materials known to those of ordinary skill in the art. In other embodiments, the flow reducing member 14 may be generally made of an elastomeric material, such as elastics.

According to certain embodiments, a hole 15 may be defined in the flow reducing member 14. During deployment of the apparatus 10, the guide wire may be configured to extend through the hole 15. In some embodiments, the flow reducing member 14 includes means to partially, substantially, or totally block the hole 15 when the guide wire is removed therefrom. In one or more embodiments, swelling material may be disposed in or about the hole 15 or on a portion of the flow reducing member 14 adjacent the hole 15. Upon coming into contact with fluids, the swelling material, and possibly the portion, may expand to substantially or totally block the hole 15. For example, the portion of the flow reducing member 14 adjacent the hole 15 may include a pocket configured to hold or otherwise store the swelling material until needed. In some embodiments, the swelling material may include microparticles. In other embodiments, the swelling material may be hydrogel or other suitable swelling materials known to those skilled in the art. When fluid, such as blood, contacts the swelling material, the swelling material and the pocket may expand (e.g., up to 3 to 5 times their initial size) to substantially block the hole 15.

According to certain embodiments, the flow reducing member 14 forms a continuous cover without using the flap 78. For example, the flow reducing member 14 may form a cover that is generally disposed over the exterior surface of the distal portion 24, thereby covering the distal opening 16. In some embodiments, the flow reducing member 14 is made of a self-sealing material, which allows for an extension of the guide wire to extend therethrough while maintaining a fluid-tight seal. Once the guide wire is removed, the flow reducing member 14 may self-seal and maintain the fluid-tight seal about the distal opening 16. In some embodiments, the flow reducing member 14 may define a plurality of pores used to occlude particular fluids, such as, blood. In one embodiments, the pores may have a diameter ranging between about 5 microns and about 10 microns. In other embodiments, the pores may have a diameter that is less than about 5 microns or greater than about 10 microns, less than about 3 microns, or less than about 1 micron. In yet other embodiments, the pores may have a diameter that is greater than about 13 microns or greater than about 16 microns.

Although the flow reducing member 14 is depicted in FIG. 1 as being disposed over or about the distal portion 24, the flow reducing member 14 may be disposed over other portions of the frame 76, without departing from the scope of the disclosure. For example, the flow reducing member 14 may be disposed over the proximal portion 20, middle portion 22, or a combination of both. In another example, flow reducing member 14 may be disposed over the entirety or portions of each of the proximal, middle, and distal portions 20, 22, 24.

In some embodiments, the frame 76 may have a length ranging between about 7 millimeters (mm) and about 9 mm. In other embodiments, the length of the frame 76 may be less than about 7 mm or greater than about 9 mm. According to certain embodiments, a combined length of the proximal and middle portions 20, 22 may range between about 4 mm and about 5 mm to provide adequate anchoring of the frame 76 with respect to the distal portion 24 (e.g., between about 40% and about 70% of the length of the frame 76). In some embodiments, the combined length of proximal and middle portions 20, 22 may be less than about 4 mm or greater than about 5 mm. In some embodiments, the distal portion 24 may have a length ranging between about 3 mm and about 4 mm. In other embodiments, however, the length of the distal portion 24 may be less than about 3 mm or greater than about 4 mm.

In some embodiments, a diameter of the proximal portion 20 and/or the middle portion 22 may be between about 2 mm and about 10 mm. In other embodiments, the diameter of the proximal portion 20 and/or the middle portion 22 may be less than about 2 mm or greater than about 10 mm. In some embodiments, a diameter of the distal portion 24 may be between about 0.4 mm and about 0.5 mm. In other embodiments, the diameter of the distal portion 24 may be less than about 0.4 mm or greater than about 0.5 mm.

In some embodiments, an average thickness of the flow reducing member 14 is between about 0.0005 inches and about 0.006 inches. In other embodiments, the average thickness of the flow reducing member 14 may be less than about 0.0005 inches or greater than about 0.006 inches. In certain embodiments, an average thickness of the distal portion 24 is greater than an average thickness of the proximal portion 20. As can be appreciated, such a configuration may ensure that flow is reduced at the distal portion 24 near the distal opening 16. In some embodiments, the average thickness of the distal portion 24 is between about 0.002 inches and about 0.012 inches. In other embodiments, the average thickness of the distal portion 24 may be less than about 0.002 inches or greater than about 0.012 inches. In some embodiments, the average thickness of the proximal portion 20 is between about 0.0005 inches and about 0.006 inches. In other embodiments, however, the average thickness of the proximal portion 20 may be less than about 0.0005 inches or greater than about 0.006 inches.

According to various aspects of the subject technology, the apparatus 10 may be used to reduce or stop flow through a tubular structure of a patient. The apparatus 10 may be used for rapid, well-controlled, and reliable occlusion of various tubular structures. As used herein, "tubular structure" may refer to at least one of a blood vessel, a fallopian tube, a cervical canal, a vagina, a cervix, a vas deferens, a bronchus, a ureter, a colon, a rectum, an anus, a bile duct, a pancreatic duct, or other muscular ducts or tubing found in the human body. In some embodiments apparatus 10 may be used as a birth control (contraceptive) device. Such use may allow for reversible contraception without surgery. In some embodiments, the apparatus 10 may be used for temporary occlusion in cases of lung disease, or for temporary occlusion of female reproductive organs for contraceptive purposes. In some embodiments, the apparatus 10 may be removed, or flow may be restored through the tubular structure to restore original organ functions.

In some embodiments, the apparatus 10 may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or fallopian tubes for minimally-invasive contraceptive intervention, endovascular occlusion of varicocele in males and low abdominal gonadal veins for reducing or completely eliminating chronic pelvic pain syndrome in females). In some embodiments, the apparatus 10 may be used for stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, the apparatus 10 may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, the apparatus 10 may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of uretero-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). As will be appreciated, use of the apparatus 10 is not limited to applications for human patients, but may also include veterinary applications, without departing from the scope of the disclosure.

In some embodiments, the apparatus 10 may further include a tube (not shown) configured to extend through the flow reducing member 14 and the distal opening 16 to be positioned at, for example, a target site of the patient. The apparatus 10 may also be communicably coupled to a vacuum source (not shown) configured to apply a vacuum through the tube for removing at least one of emboli and fluid from the target site. For example, the tube may be placed in a diseased area that has been subjected to occlusion, and the tube may be used to remove bodily fluids and/or solid components (e.g., blood clots) from the diseased area.

Figure 2:
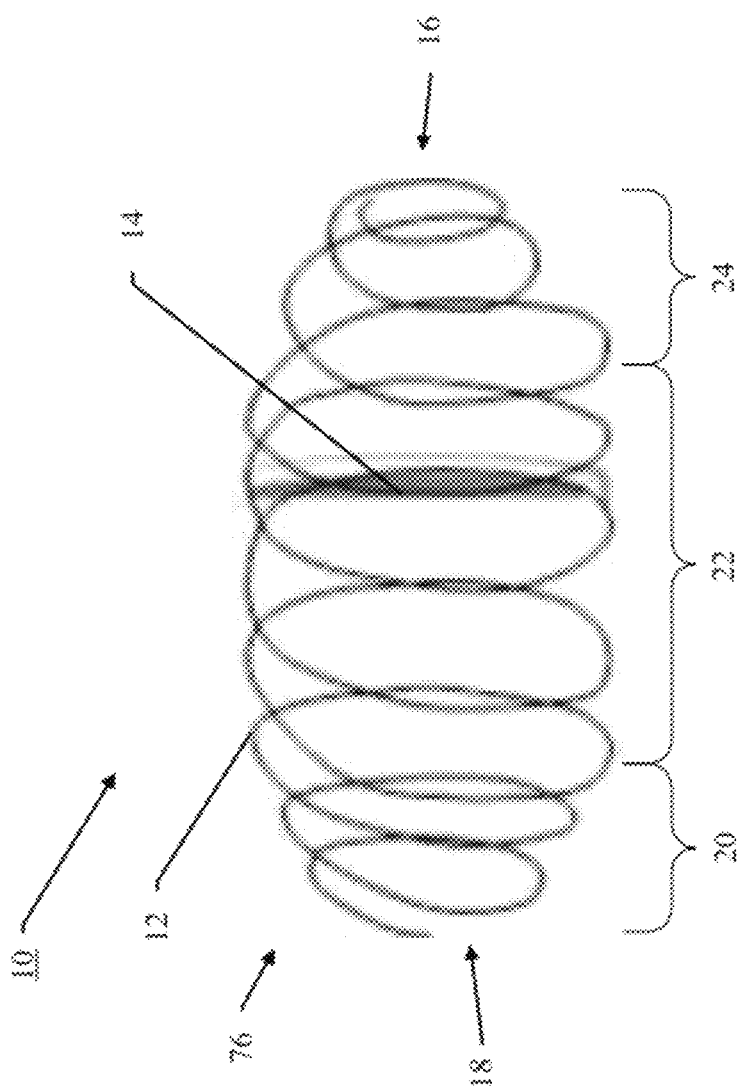
FIG. 2 illustrates an example of an apparatus, in accordance with various embodiments of the subject technology.

FIG. 2 illustrates an example of apparatus 10, in accordance with various embodiments of the subject technology. In some embodiments, the proximal portion 20 is tapered such that the outer cross-sectional dimension of the proximal opening 18 is less than the outer cross-sectional dimension of the middle portion 22. Tapering the proximal portion 20 provides several advantages. For example, the apparatus 10 may be deployed within a lumen of a tubular structure of a patient, and removing or repositioning the apparatus 10 within the lumen may cause the apparatus 10 to shift axially within the lumen. In removing the apparatus 10 from within the lumen, a catheter (not shown) may be placed proximal to the apparatus 10 to receive the apparatus 10. While the apparatus 10 is being removed, such as by inversion as described above, the apparatus 10 may shift proximally. Thus, the tapering of proximal portion 20 may ensure that apparatus 10 shifts into the catheter when apparatus 10 is being removed.

As shown in FIG. 2, the flow reducing member 14 may be disposed or otherwise arranged inside of the frame 76. Specifically, the flow reducing member 14 may be disposed in the interior of the frame 76 and coupled to the middle portion 22. In this configuration the flow reducing member 14 may be configured to occlude the tubular structure when the apparatus 10 is disposed within the lumen of the tubular structure. Because the middle portion 22 includes portions of the frame 76 that are adapted to expand and engage the inner surface of the lumen, the flow reducing member 14 may be configured to stretch or otherwise expand correspondingly in order to properly occlude the tubular structure.

When used to occlude the tubular structure, the flow reducing member 14 may capture emboli or other particles flowing through the lumen of the tubular structure. Because the ends at both the proximal and distal portions 20, 24 are tapered, the emboli or other particles may be contained or otherwise trapped within the frame 76. For example, the flow reducing member 14 may be used to reduce or stop blood flow in a vessel, thereby resulting in clotting of the blood. In some embodiments, the blood clot(s) may be trapped within the interior of the frame 76 between the tapered proximal portion 20 and the flow reducing member 14, such that the blood clot is prevented from flowing proximally out of the frame 76.

According to certain embodiments, the outer cross-sectional dimension of the proximal opening 18 may be larger than the outer cross-sectional dimension of the distal opening 16, which may be useful for achieving a reduction or stoppage of flow through the distal opening 16.

Figure 3:
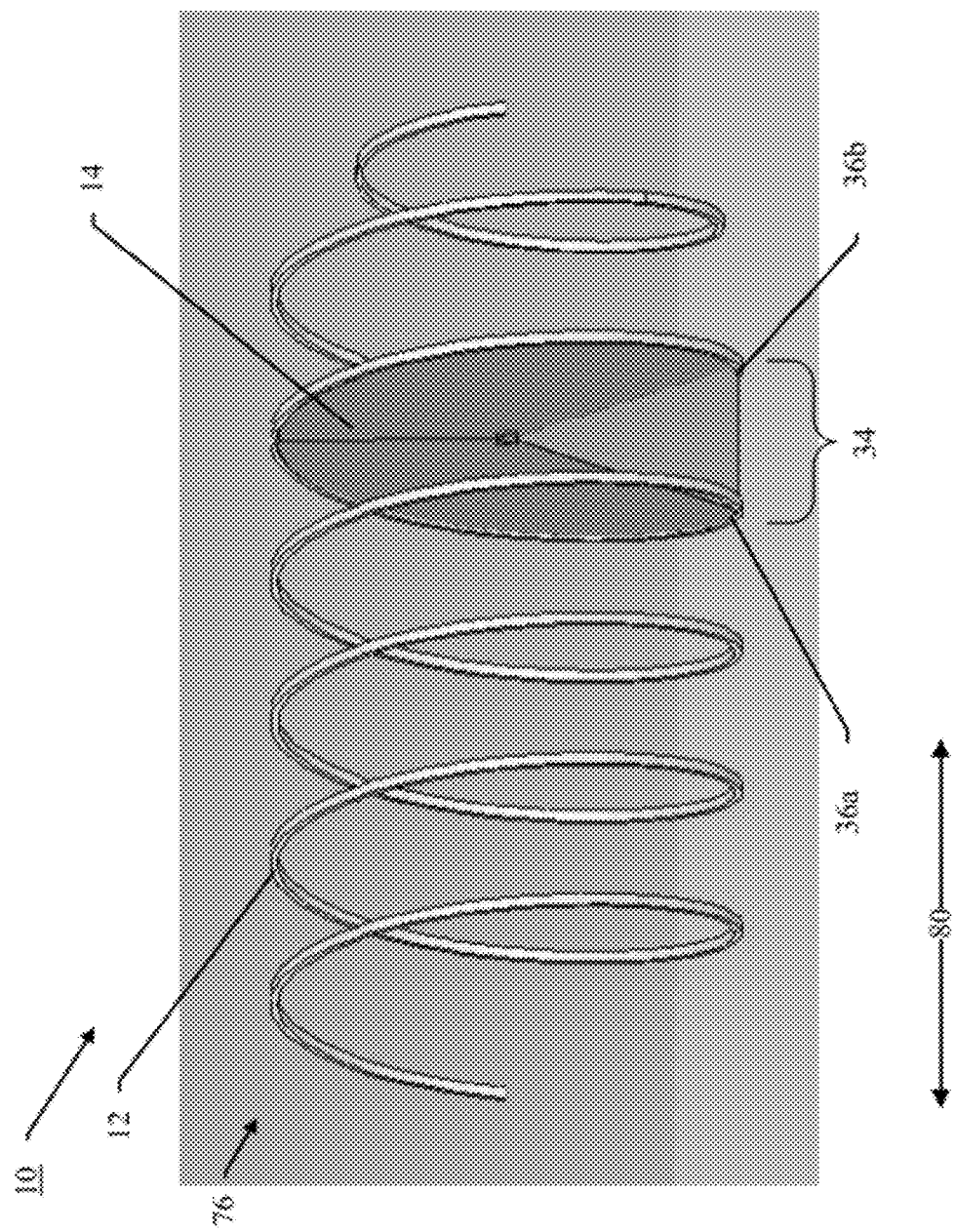
FIG. 3 illustrates an example of an apparatus having a flow reducing member disposed in an interior of a frame, in accordance with various embodiments of the subject technology.

Referring now to FIG. 3, illustrated is an example of the apparatus 10 wherein the flow reducing member 14 is disposed within the frame 76, in accordance with various embodiments of the subject technology. As shown, the flow reducing member 14 may be coupled to one or more coils 34 of the frame 76 such that the flow reducing member 14 substantially encompasses the opening defined by the coil 34. In one or more embodiments, the coil 34 is formed by a portion of the elongate member 12, extending from point 36a to point 36b, and the flow reducing member 14 is coupled or otherwise attached to the elongate member 12 from point 36a to point 36b. As can be appreciated, when the flow reducing member 14 is coupled to the coil 34, the opening defined by the coil 34 may be substantially or entirely occluded.

In certain embodiments, the thickness or axial depth of the coil 34 (i.e., a first coil), as measured along an axial dimension 80 of first frame 76, may be less than the thickness or axial depth of another (second) coil of the frame 76. Having a decreased axial depth may beneficially allow the flow reducing member 14 to span the opening through the coil 34 without being stretched too far along the axial dimension 80 and thereby cause tears or weakened portions of the flow reducing member 14.

Figure 4:
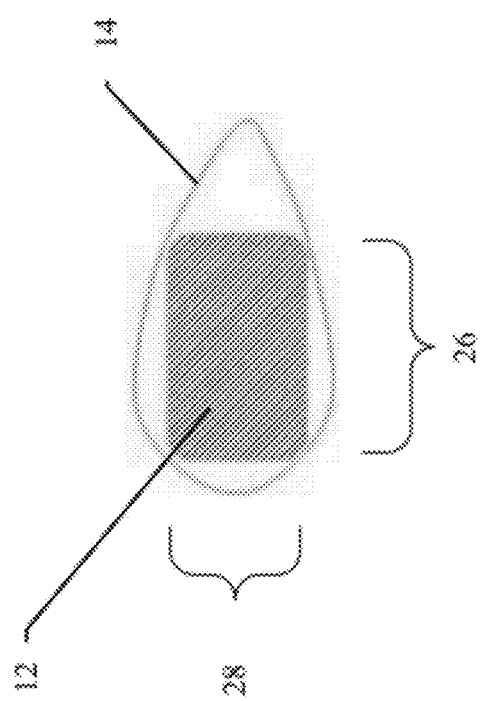
FIG. 4 illustrates a cross-sectional dimension of an elongate member, in accordance with various embodiments of the subject technology.

FIG. 4 illustrates a cross-sectional view of the elongate member 12, in accordance with various embodiments of the subject technology. In some embodiments, the elongate member 12 may exhibit a substantially rectangular cross-section. It was found that such a cross-section stabilized the apparatus 10 within a lumen of a tubular structure, thereby minimizing its axial shifting once deployed within the lumen. The substantially rectangular cross-section also provides additional strength for preventing the frame 76 from collapsing under the various forces exerted by the lumen. The rectangular cross-section also allows the elongate member 12 to be easily arranged or otherwise formed into the spiral configuration to form the frame 76.

In some embodiments, the corners of the rectangular cross-section are radiused or arcuate. In some embodiments, the length 26 of the rectangular cross-section is between about 0.008 inches and about 0.014 inches. In other embodiments, the length 26 may be less than about 0.008 inches or greater than about 0.014 inches. In some embodiments, the width 28 of the rectangular cross-section is between about 0.004 inches and about 0.006 inches. In other embodiments, the width 28 may be less than about 0.004 inches or greater than about 0.006 inches.

According to certain embodiments, the flow reducing member 14 may be coupled to the elongate member 12 as shown in FIG. 4. For example, the flow reducing member 14 may wrap around or otherwise be disposed about the elongate member 12. Accordingly, the flow reducing member 14 may form a drum-like cover. In other embodiments, as shown in FIG. 3 above, the flow reducing member may extend through an opening defined by one or more coils 34.

FIGS. 5A and 5B illustrate the apparatus 10 as deployed within a lumen 30 of a tubular structure of a patient, in accordance with various embodiments of the subject technology. For simplicity, the frame 76 is illustrated in outline form, but otherwise includes one or more of the variations described herein. As illustrated, the flow reducing member 14 may be coupled to an interior surface 17 of the frame 76 at or near the middle portion 22. One benefit of having the flow reducing member 14 coupled to the middle portion 22 is that the flow reducing member 14 may be provided with enough axial space to stretch proximally or distally depending on the direction of the flow 32. For example, as shown in FIG. 5A, the flow 32 is in the proximal direction, and hence, the flow reducing member 14 may also be stretched distally. As shown in FIG. 5B, flow 32 is in the distal direction, and hence, the flow reducing member 14 may be stretched distally. Consequently, by coupling the flow reducing member 14 to the middle portion 22 of the frame 76, the flow reducing member 14 may be used to reduce or stop the flow 32 through the lumen 30 in either direction.

Figure 6:
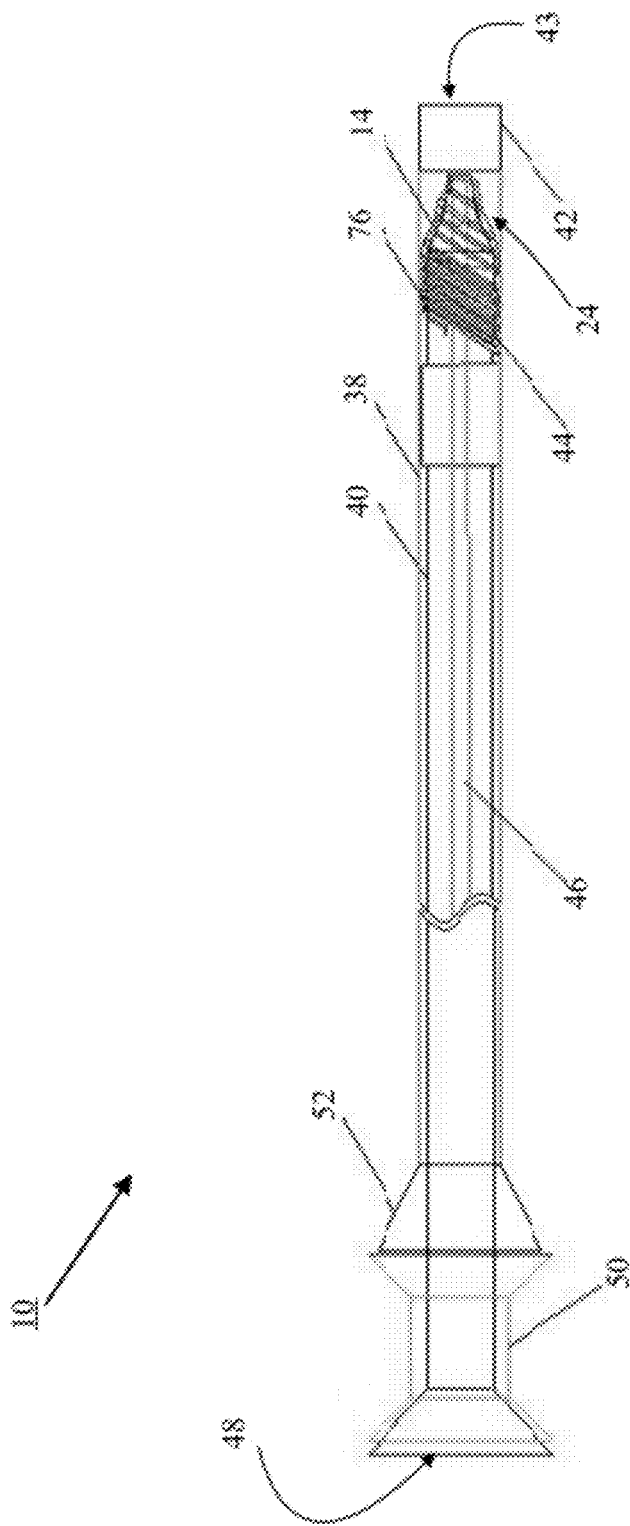
FIG. 6 illustrates an example of a frame and a flow reducing member being positioned within an outer catheter, in accordance with various embodiments of the subject technology.

Referring now to FIG. 6, illustrated is an example of the apparatus 10 as arranged within a catheter for delivery, in accordance with various embodiments of the subject technology. As used herein, the term "catheter" may be given at least its ordinary meaning, but may also refer to any elongate member having a lumen passing axially therethrough. Accordingly, a "catheter" can be tubular and have various suitable cross-sectional shapes, such as circular, elliptical, polygonal (e.g., triangular, rectangular, hexagonal, octagonal, etc.), combinations thereof, or the like. The apparatus 10 may include an outer catheter 38 configured to be positioned within a lumen at a first deployment site, and an inner catheter 40 disposed within the outer catheter 38. The outer catheter 38 may have a tip 42 arranged at its distal end, and a distal opening 43 defined therein. The tip 42 may be a soft tip adapted to reduce or otherwise prevent trauma and/or friction when the outer catheter 38 is being navigated through the lumen to the first deployment site. The frame 76 may be configured to interpose the outer and inner catheters 38, 40 during delivery and before the frame 76 is deployed for use within the lumen. As shown in FIG. 6, the flow reducing member 14 may be disposed over the distal portion 24 of frame 76, and a guide wire 46 may be configured to extend through the inner catheter 40 and the distal opening 16 (FIG. 1) of the frame 76.

A proximal handle 48 may be coupled to the proximal end of the inner catheter 40. The frame 76 and the flow reducing member 14 may be deployed from the outer catheter 38 by forcing the proximal handle 48 and the inner catheter 40 distally relative to the outer catheter 38 and until the frame 76 and the flow reducing member 14 extend beyond the distal opening 43 and into the lumen.

In some embodiments, the apparatus 10 may include a security block 50 coupled to the proximal handle 48. The security block 50 may be configured to stop the axial translation of the proximal handle 48 such that the inner catheter 40 does not extend beyond what is required to properly deploy the frame 76 and the flow reducing member 14. In one or more embodiments, the security block 50 may have a predetermined axial length and be configured to bias a proximal portion 52 of the outer catheter 38 when the proximal handle 48 has translated sufficiently to fully the deploy frame 76 and the flow reducing member 14. In some embodiments, when the security block 50 stops axial translation of the proximal handle 48, the user may understand that the frame 76 and the flow reducing member 14 has been fully deployed from the outer catheter 38, so it may serve as an indicator of full deployment.

FIGS. 7A and 7B illustrate enlarged views of the frame 76 and the flow reducing member 14 as positioned within the outer catheter 38, in accordance with various embodiments of the subject technology. In some embodiments, the inner catheter 40 defines a series of threads 44 at its distal end, and the frame 76 may be threaded onto the series of threads 44 in order to secure the elongate member 12 to the inner catheter 40. The series of threads 44 may be made of nylon, metal, or other suitable material known to those of ordinary skill in the art. In some embodiments, the flow reducing member 14 may be of a suitable radial thickness to interpose the outer surface 45 of the inner catheter 40 and an inner surface 47 of the outer catheter 38. For example, an average radial thickness of the flow reducing member 14 may be between about 0.0005 inches and about 0.006 inches, or other suitable ranges.

The outer catheter 38 generally prevents the frame 76 from expanding radially when the frame 76 is secured between the inner surface 47 of the outer catheter 38 and the outer surface 45 of the inner catheter 40. As the inner catheter 40 shifts until the frame 76 extends beyond the distal opening 43 of the outer catheter 40, the outer catheter 38 no longer prevents the frame 76 from radially expanding. As a result, the frame 76 may expand from an undeployed (compressed) configuration into a deployed (expanded) configuration such that the frame 76 engages an inner surface of the tubular structure. In some embodiments, the frame 76 does not automatically expand into its deployed configuration but is instead expanded into the deployed configuration with a balloon or other expansion-inducing device. In some embodiments, however, the frame 76 may be self-expandable.

According to various embodiments of the subject technology, the frame 76 and the flow reducing member 14 are capable of being deployed at the deployment site, resheathed within the catheter 38, repositioned at the deployment site, and redeployed. For example, if an operator decides that an initial placement of the frame 76 and the flow reducing member 14 is incorrect or otherwise undesirable, the operator may redeploy and/or reposition the frame 76 and the flow reducing member 14. To accomplish this, the inner catheter 40 may be configured to shift distally relative to the outer catheter 38 until at least a portion of the frame 76 extends beyond the distal opening 43 of the outer catheter 38 and into a first deployment site where the frame 76 is partially deployed. Subsequently, the inner catheter 40 may be configured be retracted proximally relative to outer catheter 38 until the frame 76 is again resheathed within the outer catheter 38. Since a proximal portion of the elongate member 12 (e.g. the frame 76) is still secured to the series of threads 44, the frame 76 is also retracted once the inner catheter 40 is retracted. Once resheathed, the outer catheter 38 may be moved to the correct (second) deployment site for correctly deploying the frame 76. The process described above is repeated to redeploy the frame 76 from the outer catheter 38 and into the second deployment site.

In some embodiments, the apparatus 10 may also include one or more stops, depicted in FIGS. 7A and 7B as a first stop 54a and a second stop 54b. The stops 54a,b may be generally disposed between the outer catheter 38 and the inner catheter 40 and configured to prevent the frame 76 from moving proximally relative to at least one of the outer catheter 38 and the inner catheter 40. In some embodiments, the second stop 54b is coupled to the inner surface 47 of the outer catheter 38 and the first stop 54a may be coupled to the outer surface 45 of the inner catheter 40, or vice versa. The stops 54a,b may be annular or may be defined by one or more protrusions extending from the respective surfaces 45, 47. In operation, when the inner catheter 40 moves distally relative to the outer catheter 38 in order to deploy the frame 76, the first stop 54a axially engages the second stop 54b, thereby preventing the inner catheter 40 from advancing further relative to the outer catheter 38.

Figure 8:
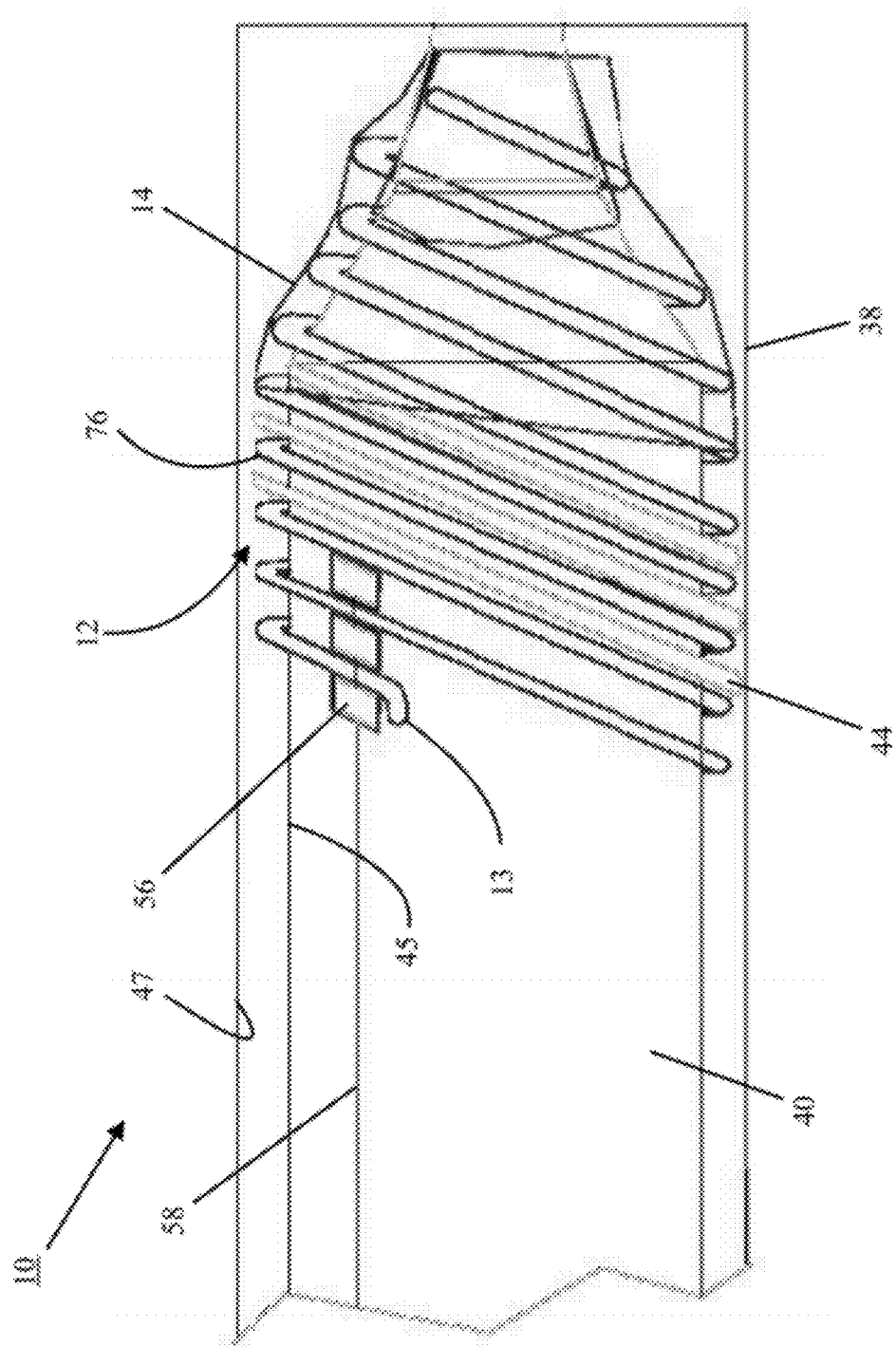
FIG. 8 illustrates an example of a frame and a flow reducing member positioned within an outer catheter, in accordance with various embodiments of the subject technology.

FIG. 8 illustrates an enlarged view of the exemplary frame 76 and flow reducing member 14 as positioned within the outer catheter 38, in accordance with various embodiments of the subject technology. In some embodiments, the apparatus 10 may further include one or more blocks 56 disposed on or otherwise coupled to the outer surface 45 of the inner catheter 40 such that the elongate member 12 (e.g., the frame 76) wraps around the one or more blocks 56 to secure the elongate member 12 to the inner catheter 40. In some embodiments, the one or more blocks 56 are made of an electroactive polymer (EAP) and are configured to swell when electric signals are applied thereto. In one or more embodiments, when the electric signals are applied to the blocks 56, the elongate member 12 may be substantially locked to the one or more blocks 56. During deployment of the elongate member 12, however, including deployment of the frame 76 and the flow reducing member 14, the electric signals are discontinued to allow the frame 76 to disengage from the one or more blocks 56. However, should repositioning be desired, the electric signals may be reapplied to the blocks 56, thereby securing a proximal portion or tip 13 of the elongate member 12 to the inner catheter 40 once more, and the inner catheter 40 may subsequently be retracted proximally, which will resheath the frame 76 into the outer catheter 38.

Figure 9:
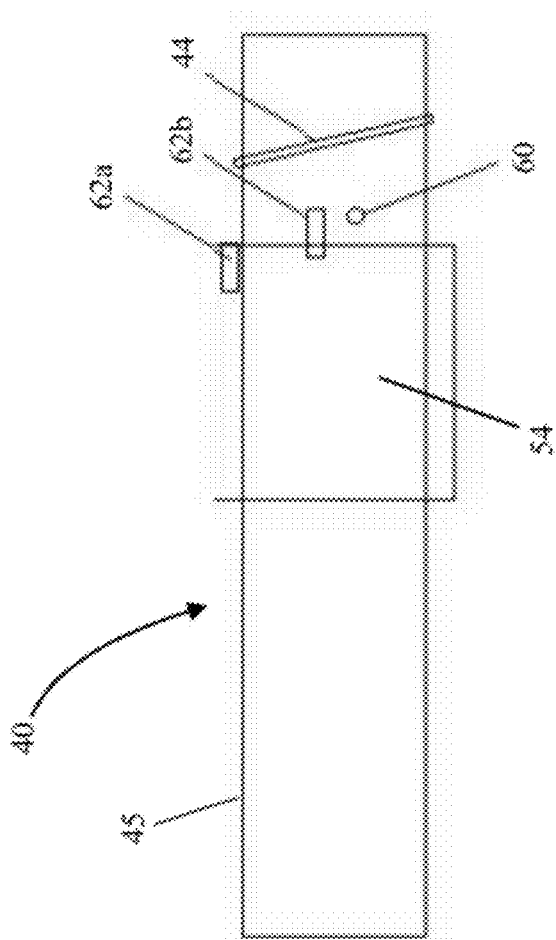
FIG. 9 illustrates an example of an inner catheter, in accordance with various embodiments of the subject technology.

FIG. 9 illustrates an enlarged view of the exemplary inner catheter 40, in accordance with various embodiments of the subject technology. In some embodiments, the inner catheter 40 defines a hole 60 in its outer surface 45. The hole 60 may be configured to receive the proximal tip 13 (FIGS. 1 and 8) of the elongate member 12 in order to secure the frame 76 to the inner catheter 40. In other embodiments, the inner catheter 40 may define one or more grooves (e.g., groove 62a and 62b) about its outer surface 45. Similar to the hole 60, the grooves 62a or 62b may be configured to receive the proximal tip 13 of the elongate member 12, thereby securing the frame 76 to the inner catheter 40. As illustrated, at least one of the grooves 62a may be formed on or otherwise defined in the first stop 54a, and other grooves 62b may be formed on the outer surface 45 of the inner catheter 40.

FIGS. 10A and 10B illustrate an example of the frame 76 and the flow reducing member 14 as positioned within the outer catheter 38, according to various embodiments of the subject technology. As shown in FIG. 10A, the flow reducing member 14 may be coupled to the middle portion 22 of the frame 76, such as being coupled to the interior surface 17 of the frame 76. Thus, when the frame 76 and the flow reducing member 14 are stowed within the outer catheter 38 during delivery, the inner catheter 40 may be configured to bias the flow reducing member 14 against the interior surface 17 of the frame 76, such as at the distal portion 24. In other embodiments, the flow reducing member 14 may be disposed over the distal portion 24 of the frame 76, as shown in FIG. 10B.

In one or more embodiments, the distal portion 24 and the flow reducing member 14 may be configured to extend beyond the distal opening 43 of the outer catheter 38 during delivery of the apparatus 10. The exposed portions of the distal portion 24 and the flow reducing member 14 may be atraumatic and prevent injury or damage to tubular structures during device tracking and delivery to the deployment site. Accordingly, when the outer catheter 38 is moved within the lumen to a deployment site, the exposed portions of the distal portion 24 and the flow reducing member 14 that extend beyond the distal opening 43 may be configured to engage the inner wall (not shown) of the lumen to reduce friction and potential vessel injury. In such a case, the tip 42 (see FIG. 6) may not be necessary. In some embodiments, the distally extended portion of the flow reducing member 14 may be extended about 2 mm beyond the distal opening 43, and the distally extended portion of the flow reducing member 14 may be extended less than about 2 or greater than about 2 mm beyond the distal opening 43.

Figure 11:
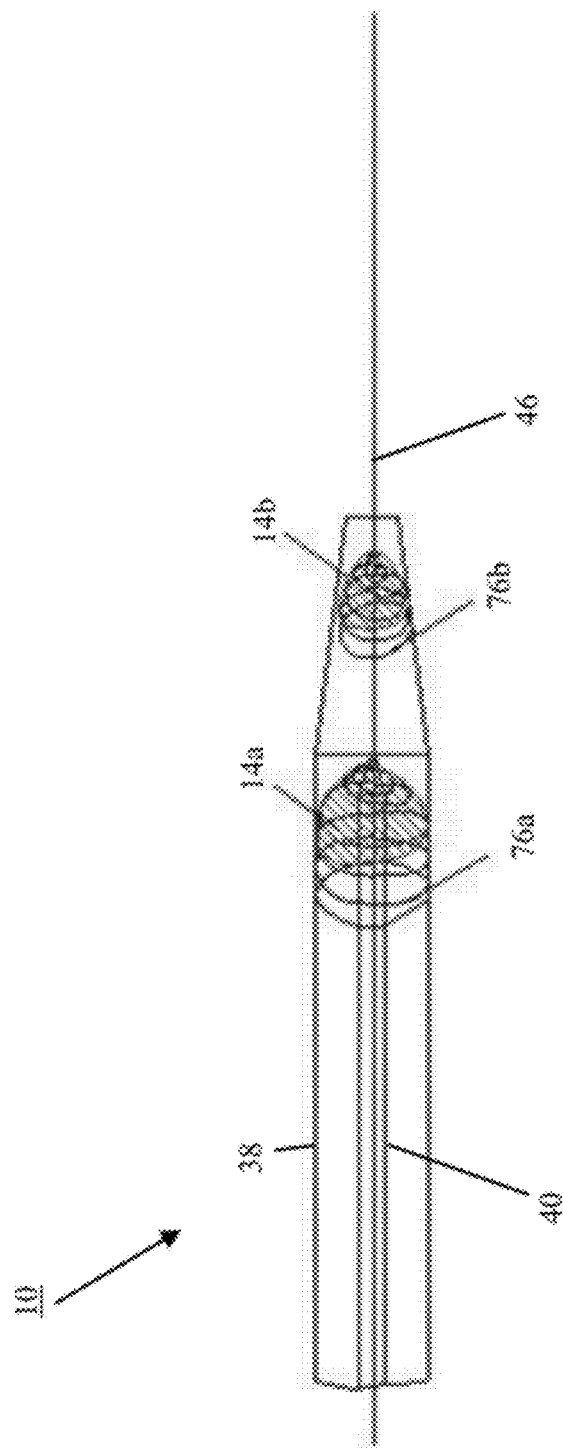
FIG. 11 illustrates an example of two frames and two flow reducing members positioned within an outer catheter, in accordance with various embodiments of the subject technology.

Referring now to FIG. 11, illustrated is another embodiment of the apparatus 10 where two frames 76 are employed, according to one or more embodiments disclosed. Specifically, illustrated are a first frame 76a and a second frame 76b, axially-spaced from the first frame 76a. The apparatus 10 in FIG. 11 may also include a first flow reducing member 14a and a second flow reducing member 14b, also positioned within the outer catheter 38 in conjunction with the first and second frames 76a,b, respectively. Accordingly, the apparatus 10 may be configured to implant or otherwise deploy two frames 76a,b and corresponding flow reducing members 14a,b within a lumen. As can be appreciated, multiple frames 76a,b and flow reducing members 14a,b deployed from the same outer catheter 38 may serve to simplify surgery techniques to implant these devices. For example, significant amounts of time and effort may be saved by deploying the pair of frames 76a,b and flow reducing members 14a,b from the same outer catheter 38.

In some embodiments, the second frame 76b is configured to be positioned between the outer catheter 38 and the guide wire 46 for stowing the frame 76b prior to its deployment. The second frame 76b may be deployed in a manner similar to the deployment of the first frame 76a, as generally described above. In other embodiments, however, the second frame 76b may secured to the guide wire 46 by, for example, threading the second frame 76b to the outer surface of the guide wire 46. In yet other embodiments, the second frame 76b may be coupled to the guide wire 46 without threads, but instead using other means known in the art. For example, the second frame 76b may be coupled to the guide wire 46 using the one or more blocks made of EAP and configured to swell when electric signals are applied to the one or more blocks, as generally described above with reference to FIG. 8.

In certain embodiments, the flow reducing members 14a,b may be disposed over various portions of the frames 76a,b, respectively, depending on their desired applications. For example, the flow reducing members 14a,b may be disposed over respective distal portions of the frame 76a,b, or the first flow reducing member 14a may be disposed over the distal portion of the first frame 76a while the second flow reducing member 14b may be disposed over the proximal portion of the second frame 76b, or combinations thereof.

Figure 12:
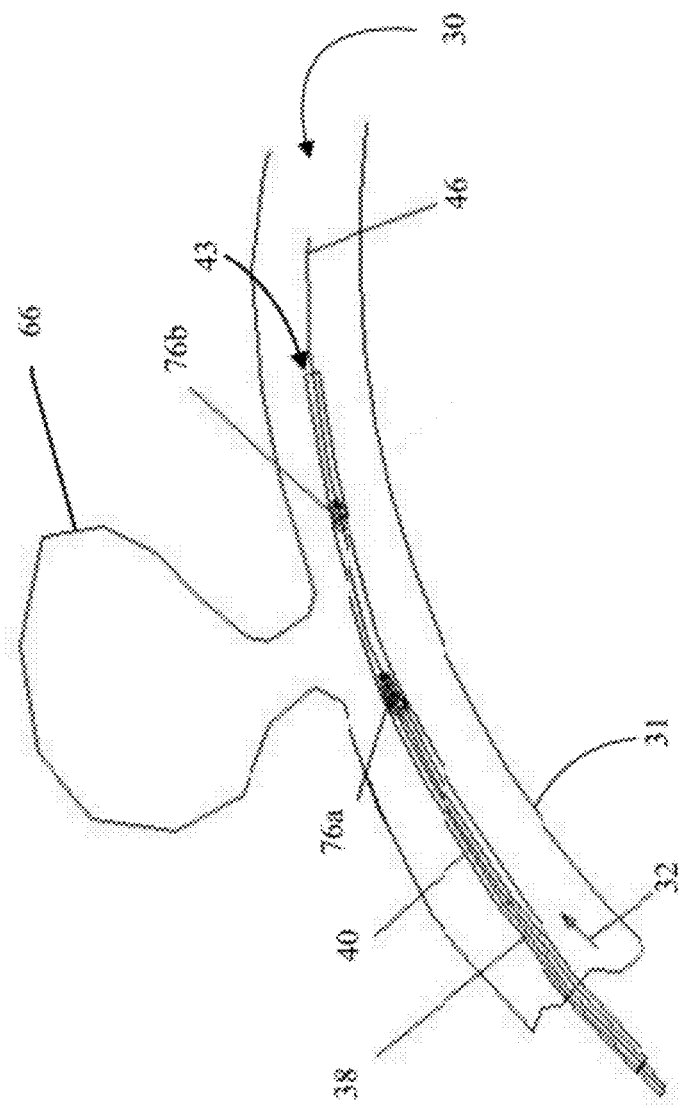
FIG. 12 illustrates an example of deploying frames, along with corresponding flow reducing members, in accordance with various embodiments of the subject technology.

FIG. 12 illustrates an exemplary method of deploying one or more frames 76 and corresponding flow reducing members 14, in accordance with various embodiments of the subject technology. The outer catheter 38 may advanced through the lumen 30 of a tubular structure 31 (e.g., blood vessel) until positioned adjacent a first deployment site, such as at an aneurysm 66, where the second frame 76b is to be deployed. In one or more embodiments, the first deployment site may be distal the aneurysm 66. The guide wire 46 is advanced distally relative to the outer catheter 38 until the second frame 76b extends beyond the distal opening 43 of the outer catheter 38 and into the first deployment site. In some embodiments, the second frame 76b may also be partially deployed, retracted (i.e., resheathed within the catheter 38), and repositioned in a manner similar to frame 76a. After the second frame 76b is properly deployed, the outer catheter 38 may then be positioned within the lumen 30 at a second deployment site, such as proximal the aneurysm 66, in order to deploy the first frame 76a. The inner catheter 40 may then be translated distally relative to the outer catheter 38 until the first frame 76a extends beyond the distal opening 43 of the outer catheter 38 and deploys into the lumen 30.

Figure 13:
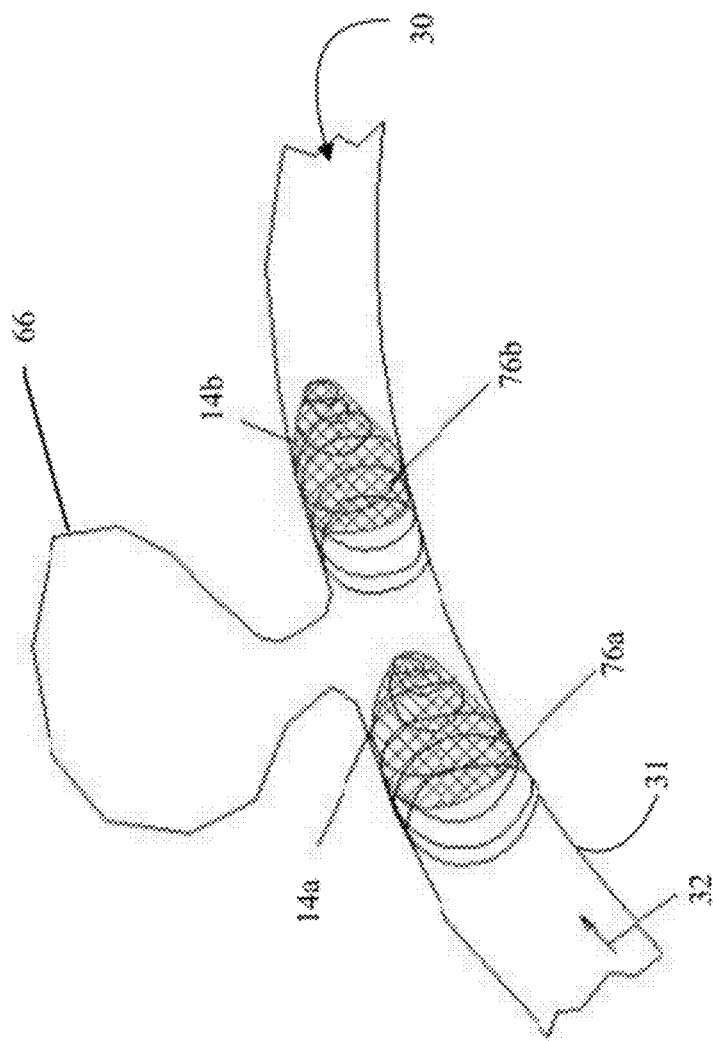
FIG. 13 illustrates an example of frames, along with corresponding flow reduction members, deployed within a lumen for occluding an aneurysm, in accordance with various embodiments of the subject technology.

Referring to FIG. 13, illustrated are the exemplary frames 76a,b and corresponding flow reduction members 14a,b deployed within the lumen 30, in accordance with various embodiments of the subject technology. In some embodiments, the second frame 76b and second flow reducing member 14b may be deployed distal the aneurysm frame 76a and flow reducing member 14a, relative to flow 32, in order to impede, reduce, or stop flow that may emanate from a direction opposite of the flow 32. The second frame 76b and second flow reducing member 14b may also be used to impede, reduce, or stop flow that may travel from within aneurysm 66, including blood clots, thereby promoting thrombosis within the aneurysm 66. In some embodiments, the flow reducing members 14a,b may be disposed over various portions of the frames 76a,b, respectively, depending on the direction of flow 32, the position of the frames 76a,b, a combination thereof, or other factors known to those in the art.

Figure 14A:
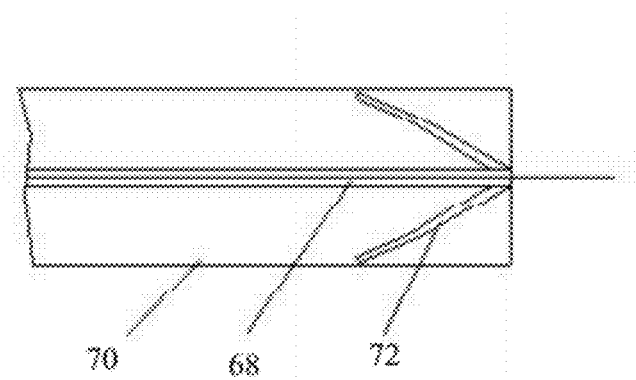
FIGS. 14A, 14B, and 14C illustrate an example of a retrieving member, in accordance with various embodiments of the subject technology.
Figure 14B:
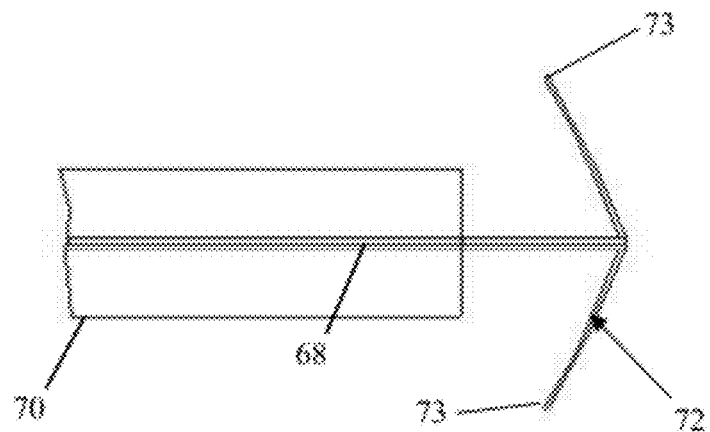
Figure 14C:
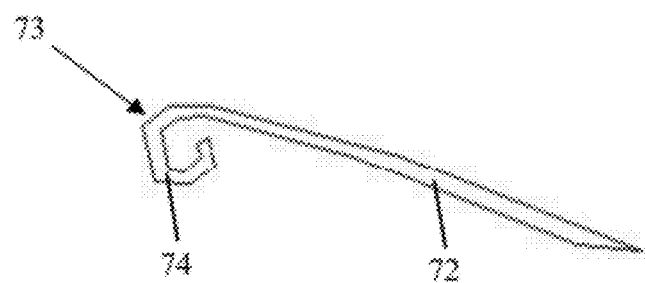

Referring now to FIGS. 14A, 14B, and 14C, illustrated is an exemplary retrieving member 68, in accordance with various embodiments of the subject technology. The retrieving member 68 may be used to remove the frame 76 and/or flow reducing member 14 from within a lumen 30. In some embodiments, the retrieving member 68 may be stowed in a compressed configuration (FIG. 14A) within a delivery catheter 70 for delivery to the frame 76 and/or flow reducing member 14 to be removed. Once deployed from the delivery catheter 70, the retrieving member 68 expands radially into a deployed configuration (FIG. 12B). In some embodiments, the retrieving member 68 is self-expanding, but in other embodiments, the retrieving member 68 may be expanded using external means.

In some embodiments, the retrieving member 68 may be advanced distally such that it extends through the flow reducing member 14. The retrieving member 68 is configured to couple to the distal portion 24 (FIGS. 1 and 2) of the frame 76 and to pull or otherwise force the distal portion 24 into the interior of the frame 76, thereby inverting the frame 76 as generally discussed above. In one or more embodiments, a separate retrieval catheter (not shown) may be positioned proximal to the site in which the frame 76 and the flow reducing member 14 are deployed for retrieving the inverted frame 76. In at least one embodiment, the delivery catheter 70 may be extendable within the retrieval catheter.

The retrieving member 68 may include one or more jaws 72 having a distal end 73 and being moveable between the compressed and deployed configurations. In some embodiments, the jaws 72 may expand radially to an angle ranging between about 45 degrees and about 60 degrees with respect to a central axis of the retrieving member 68. In one or more embodiments, the distal end 73 of each jaw 72 may include a curved portion 74, as shown in FIG. 14C. The curved portion 74 may be configured to hook or otherwise capture the distal portion 24 of the frame 76 for inverting the frame 76. In some embodiments, however, the retrieving member 68 may include other means for retrieving frame 76, such as, but not limited to, alligator clips or other pinching means adapted to grip a portion of the frame 76 for retracting and/or inverting the frame 76. In some embodiments, the retrieving member 68 may couple to the proximal tip 13 of the elongate member 12, and retrieving member 68 may be used to retract the frame 76 by applying a force in the proximal direction to the proximal tip 13, and thereby allowing for its removal through the retrieval catheter (not shown) or delivery catheter 70.

According to certain embodiments, occlusion provided by the flow reducing member 14 may be permanent or temporary. If temporary occlusion is desired, the retrieving member 68 may be used to create an opening through the flow reducing member 14 to restore flow therethrough. In some embodiments, the frame 76 may be allowed to remain in the lumen after the opening through the flow reducing member 14 has been created. This may be advantageous when occlusion is no longer desired, but the removal of the frame 76 is not necessarily a concern. In some embodiments, the flow reducing member 14 may also be removed using the foregoing techniques as described above.

Figure 15:
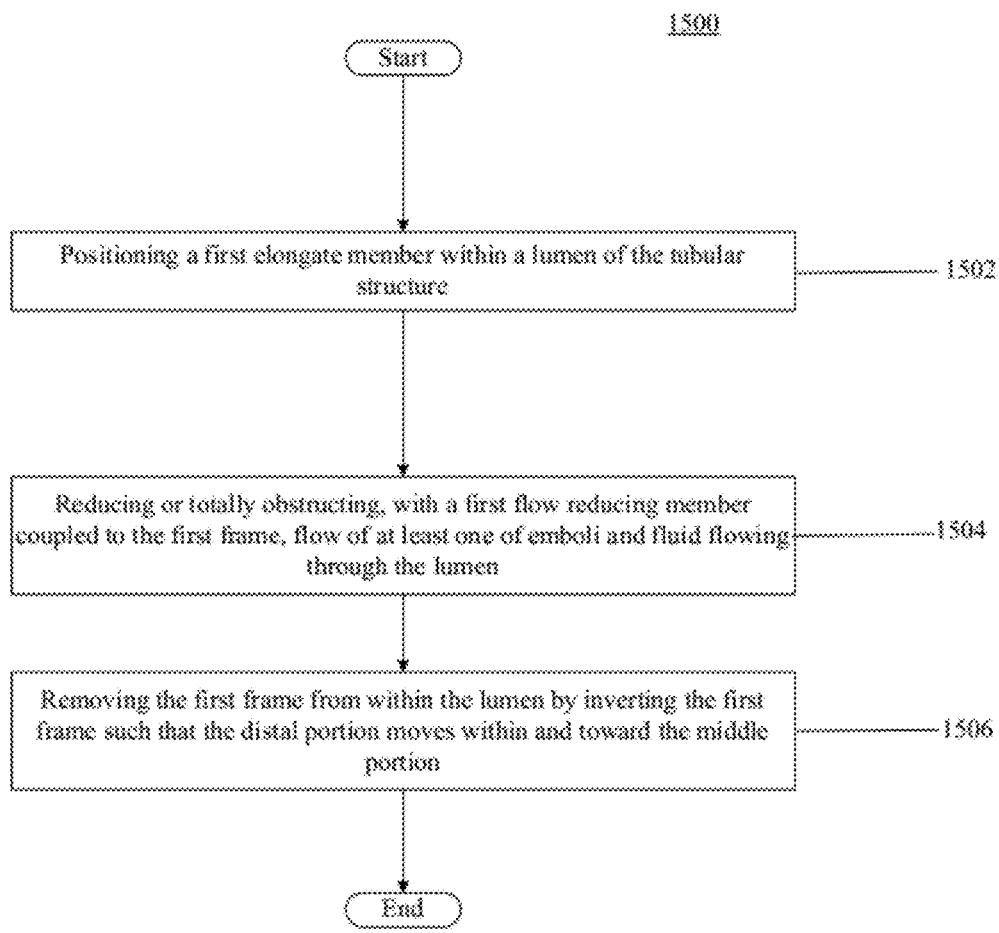
FIG. 15 illustrates an example of a method for reducing or stopping flow through a tubular structure of a patient, in accordance with various embodiments of the subject technology.

Referring to FIG. 15, illustrated is a method 1500 for reducing or stopping flow through a tubular structure of a patient, in accordance with various embodiments of the subject technology. The method 1500 may include positioning a first elongate member within a lumen of the tubular structure, as at 1502. The first elongate member may be arranged to form a first frame having a distal opening and a proximal opening. The first frame includes a proximal portion, a distal portion, and a middle portion extending therebetween. In one or more embodiments, the distal portion may be tapered such that a cross-sectional dimension of the distal opening is less than a cross-sectional dimension of the middle portion.

The method 1500 may also include reducing or totally obstructing, with a first flow reducing member coupled to the first frame, flow of at least one of emboli and fluid flowing through the lumen, as at 1504. The method 1500 may further include removing the first frame from within the lumen by inverting the first frame such that the distal portion moves within and toward the middle portion, as at 1506.

Figure 16:
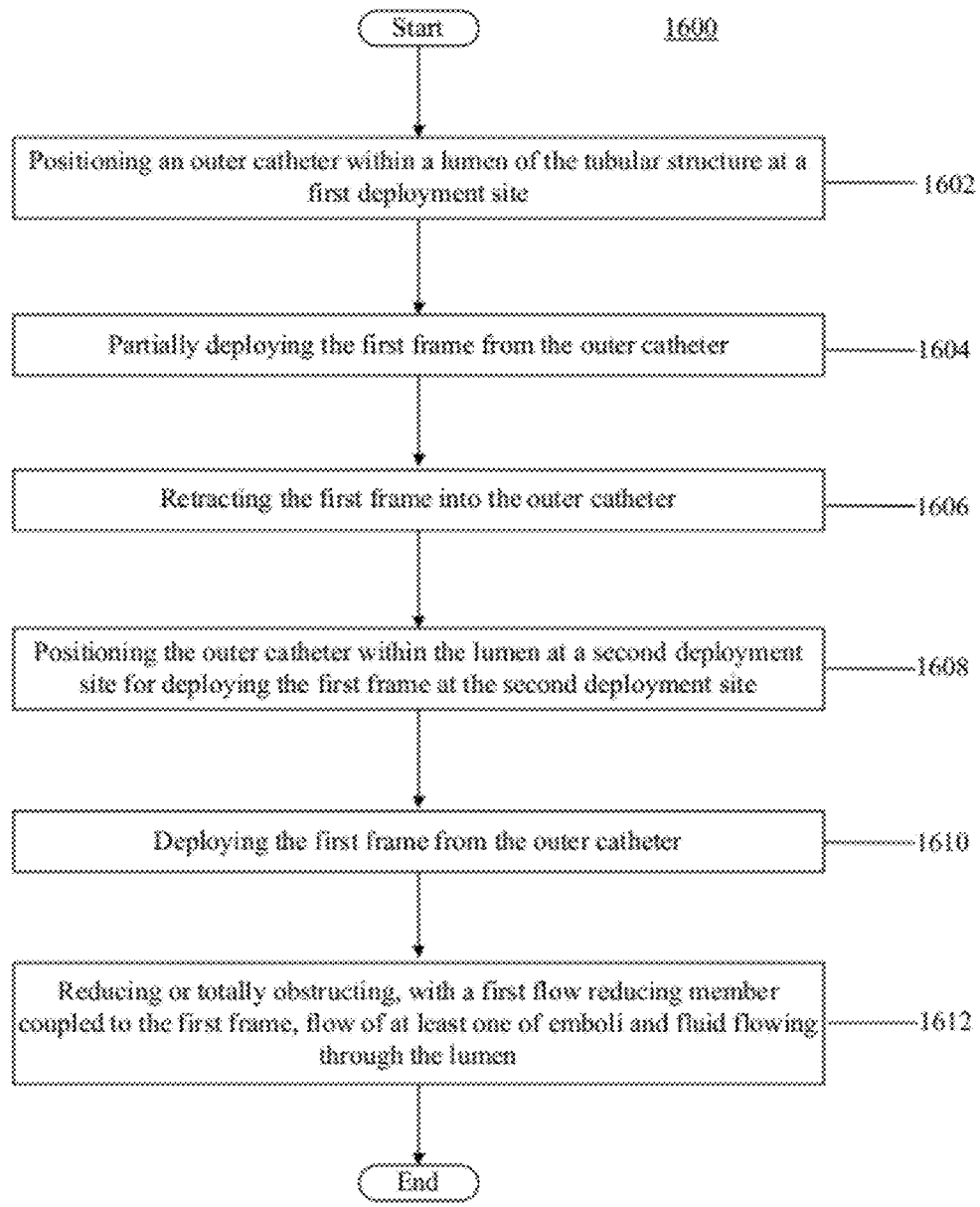
FIG. 16 illustrates an example of a method for reducing or stopping flow through a tubular structure of a patient, in accordance with various embodiments of the subject technology.

FIG. 16 illustrates another exemplary method 1600 for reducing or stopping flow through a tubular structure of a patient, in accordance with various embodiments of the subject technology. The method 1600 may include positioning an outer catheter within a lumen of the tubular structure at a first deployment site, as at 1602. An inner catheter may be disposed within the outer catheter, and a first elongate member may be interposed between the inner catheter and the outer catheter. The first elongate member forms a first frame having a distal opening and a proximal opening. The first frame further includes a proximal portion, a distal portion, and a middle portion extending therebetween. The distal portion is tapered such that a cross-sectional dimension of the distal opening may be less than a cross-sectional dimension of the middle portion.

The method 1600 may also include partially deploying the first frame from the outer catheter, as at 1604. In one or more embodiments, this may be accomplished by shifting the inner catheter distally relative to the outer catheter until a portion of the first frame extends beyond a distal opening of the outer catheter and into the first deployment site. The first frame may be retracted or otherwise resheathed into the outer catheter, as at 1606. This may be accomplished by shifting the inner catheter proximally relative to the outer catheter until the portion of the first frame is retracted proximally into the outer catheter.

The method 1600 may further include positioning the outer catheter within the lumen at a second deployment site for deploying the first frame at the second deployment site, as at 1608. The first frame may then be deployed from the outer catheter, as at 1610. In one or more embodiments, this may be accomplished by shifting the inner catheter distally relative to the outer catheter until the first frame extends beyond the distal opening of the outer catheter and into the second deployment site. The method 1600 may further include reducing or totally obstructing, with a first flow reducing member coupled to the first frame, flow of at least one of emboli and fluid flowing through the lumen, as at 1612.

In some embodiments the guide wire 46 may be absent when the frame 76 and the flow reducing member 14 are introduced. Thus, the flow reducing member 14 may lack a hole for the guide wire 46, thereby resulting in enhanced occlusion. In some embodiments, delivery of the frame 76 does not require the guide wire 46 to run through flow reducing member 14, thereby obviating the need to create a hole through the flow reducing member 14 with the guide wire 46 for delivery of the frame 76. Such embodiments are discussed in co-pending U.S. patent application Ser. No. 12/906,993, entitled "Expandable Device Delivery," filed on Oct. 18, 2010, the contents of which are hereby incorporated by reference to the extent not inconsistent with the present disclosure.

Figure 17:
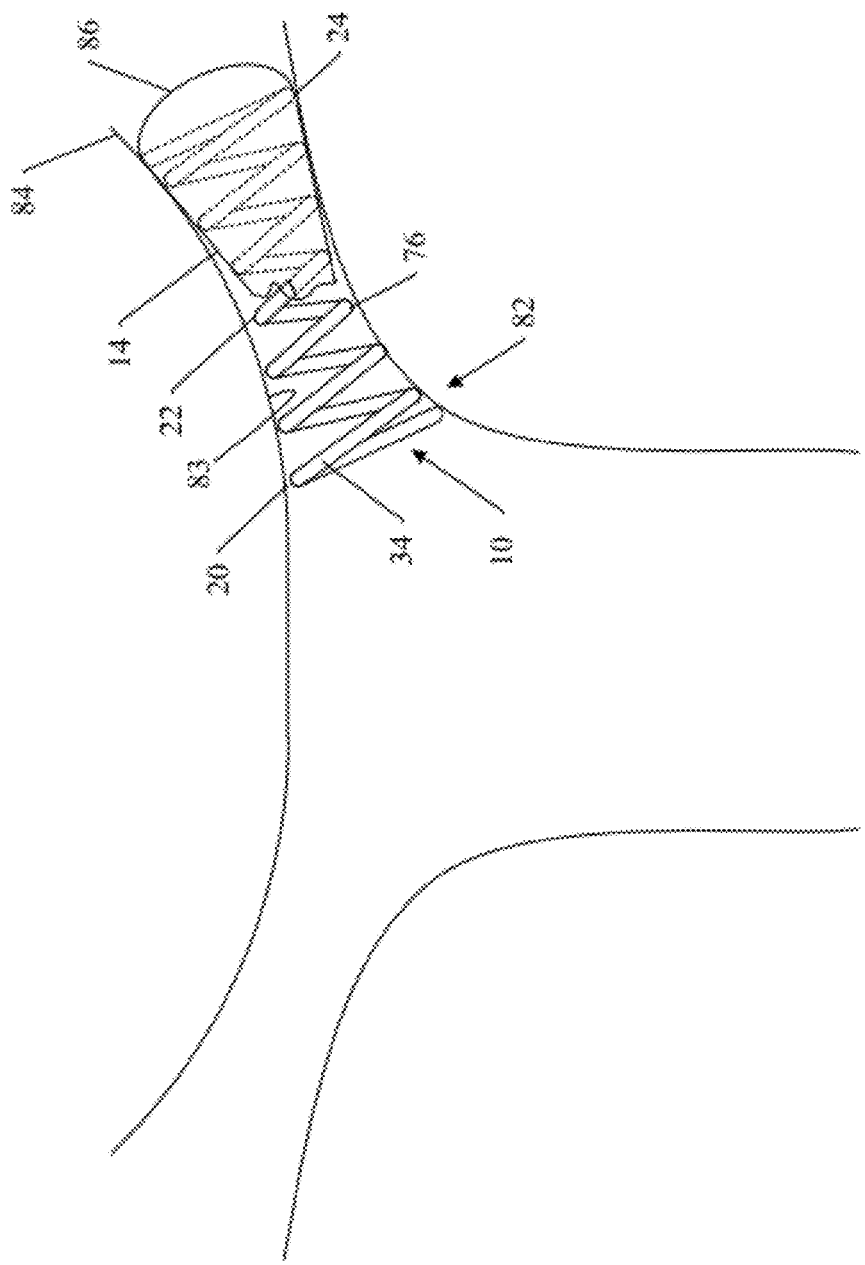
FIG. 17 illustrates an example of a reversible tubal contraceptive device placed in an isthmus of a fallopian tube, in accordance with various embodiments of the subject technology.

Referring now to FIG. 17, illustrated is another application of the apparatus 10 used, for example, as a birth control (contraceptive) device, according to one or more embodiments of the disclosure. As illustrated, the apparatus 10 may be positioned reliably and firmly into the ostium or "isthmus" 82 of a fallopian tube 84, thereby preventing the passage of sperm through the fallopian tube 84 and meeting/penetrating ovum. Similarly, the apparatus 10 may be positioned into a vas deferens (not shown) providing complete blockage of passage of sperm through the vas deferens. The apparatus 10 may alternatively be placed in any lumen of a reproductive structure of a patient through which sperm or ovum are capable of passing. The procedure for placement of the apparatus 10 in the fallopian tube 84, vas deferens, or other reproductive structure may be outpatient and minimally invasive with minimal or no use of anesthesia.

When used as a contraceptive device, the apparatus 10 may be reversible or removable, as generally described above. Thus, the apparatus 10 may be removed or otherwise inactivated per the desire of the patient. Upon reversal or inactivation, the apparatus 10 may subsequently allow passage of sperm and/or ovum through the corresponding reproductive structure. The procedure for reversal may be noninvasive or minimally invasive, non-traumatic, and/or may not involve any surgery.

Use of occlusion devices, such as the ESSURE® and ADI-ANA® devices intentionally results in scar tissue growth in fallopian tubes. Thus, such occlusion devices are considered irreversible. As can be appreciated, embodiments of the present disclosure may provide a reversible contraceptive device for use in reproductive structures (e.g., fallopian tubes, vas deferens, etc.) and may alleviate difficulties associated with scar tissue growth by preventing or otherwise ameliorating the effects of such growth while still preventing passage of sperm through particular lumens of the reproductive structures. In some embodiments, the apparatus 10 has a structural design or specific design feature(s) allowing for the retrieval of the apparatus 10 from the deployment site via a standard or specially-designed retriever. If retraction of the entire apparatus 10 from the site is precluded, for example, because of scarring tissue growth over the apparatus and/or risk of bleeding, a portion of the apparatus 10 may be removed or compromised to permit conception. For example, an occlusion cap 86 or various other adaptations of the flow reducing member 14 may be punctured, thereby effectively allowing for fluid flow within the lumen where the apparatus 10 is located. In some embodiments, the flow reducing member 14 may include an anti-inflammatory drug or other tissue-growth inhibitor. Such tissue-growth inhibitors may be used to partially or wholly coat or cover flow reducing member 14 and/or any other portion of the apparatus 10.

In some embodiments, the apparatus 10 includes materials useful for preventing or otherwise ameliorating the effects of scar tissue growth in the reproductive structures, and more particularly in lumens in which the apparatus 10 may be situated. As discussed above, utilizing properties of bioabsorbable or biodegradable materials may provide advantages. For example, bioabsorbable or biodegradable materials may have a unique quality of having been stable for a desirable period of time, such time being at least as long as the patient desires contraception. Moreover, bioabsorbable or biodegradable materials may be useful in any of a number of elements of the apparatus 10, including, but not limited to the occlusion cap 86, and/or other portions or adaptations of the flow member 14. Such materials may include materials with a plateau degradation up until a moment when degradation is triggered. In other words, the materials may have a degradation profile that is stable or "flat" until a triggering event occurs. Thus, when the patient wishes to reverse the contraception, a polymer barrier made of a bioabsorbable or biodegradable material may be removed by triggering its degradation.

Such triggering of degradation can be a well-controlled process, happening only when desired. Many methods of triggering may be used. For example, an enzyme may be used as a trigger to change or modify a surface pH of the flow reducing member 14. Another example may be via physical methods, including, but not limited to, the application of ultraviolet light, an electrical charge, a thermal charge, or another mechanical trigger to breach the flow reducing member 14, which may have a thermoset, charged, or other surface useful for selective breach. Alternatively, or additionally, the flow reducing member 14 may be constructed of a biodegradable material, covered by a removable coating configured to preserve the stability of flow reducing member 14. When the removable coating is removed, the flow reducing member 14, which may have a predetermined degradation profile, may quickly degrade or dissolve. Yet another example of triggering degradation includes the use of biostable film configured to be breached when acted upon by mechanical, electromechanical, or chemical methods and/or processes. Such methods including partial or complete degradation of the flow reducing member 14 to allow for a fluid flow channel to be restored in the reproductive structure, even when the apparatus 10 remains in place. Thus, in the event scarring tissue is present and such tissue prevents removal or retrieval of the apparatus 10, the contraceptive function of the apparatus 10 may nonetheless be reversed.

The frame 76 and the flow reducing member 14 of the apparatus 10 are described above in detail. Many features described above, such as the elongate member 12, spiral configuration, cross-sectional configuration, and other specifics may be very similar or even identical when the apparatus 10 is intended for use in contraception. However, minor modifications may offer design alternatives providing features tailored for use in reproductive structures.

Still referring to FIG. 17, when used for female contraception, the shape of the frame 76 of the apparatus 10 may allow for the proximal portion 20 to effectively anchor to the isthmus 82, with the middle portion 22 and distal portion 24 inside of the fallopian tube 84 extending distally toward an ovary (not shown). In one or more embodiments, the middle portion 22 may be free from the flow reducing member 14, with few coils 34 exposed for attaching the apparatus 10 to an inner wall 83 of the fallopian tube 84. The flow reducing member 14, including the occlusion cap 86, may be disposed about the distal portion 24 and may contact the inner wall 83 of the fallopian tube 84, thereby securing itself together with frame 76 to the fallopian tube 84.

The frame 76 may have tapered middle portion 22, with a cross-sectional dimension that is less than the outer cross-sectional dimensions of the corresponding distal and proximal portions 24, 20. In some embodiments, the narrowed middle portion 22 may engage the inner wall 83 of the fallopian tube 84. In other embodiments, however, the narrowed middle portion 22 may be configured to be offset a short distance from the inner wall 83. Such design may allow for the proximal and distal portions 20, 24 to provide an anchoring effect to the fallopian tube 84, thereby substantially preventing distal movement of the apparatus 10. Moreover, tapering of the middle portion 22 may provide an arrangement to secure complete and effective blockage when contraception is desired, while allowing cilia to remain intact and properly aligned for subsequent functioning to "push" embryos through the fallopian tube 84 after the apparatus 10 is removed or otherwise inactivated. When used for male contraception, the frame 76 may have a shape similar to that described above for female contraception, with optional modifications to accommodate differences between the fallopian tube 84 and the vas deferens (not shown).

The flow reducing member 14 may be made from a thin polymeric film. The flow reducing member 14 may be expandable, such that it covers the distal portion 24 of the frame 76, the proximal portion 20 of the frame 76, and/or most or all of the frame 76. The flow reducing member 14 may be disposed about the frame 76, disposed within the frame 76, or partially disposed on or in the frame 76. For example, the flow reducing member 14 may form a plug, diaphragm, cap, or other feature to impede, reduce, or stop passage of sperm or ovum therethrough.

Figure 18:
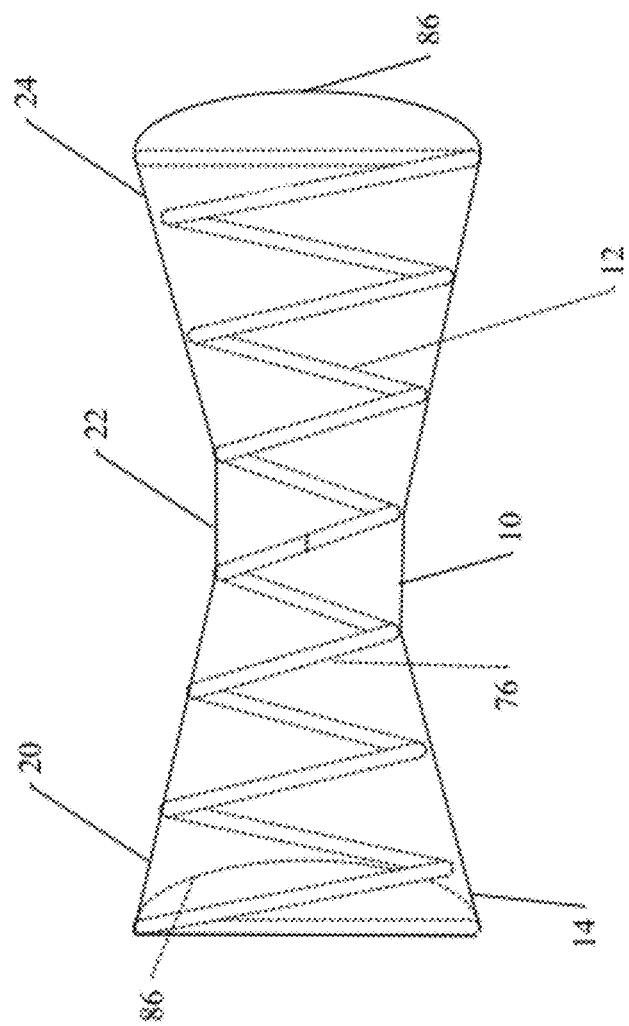
FIG. 18 illustrates a side view of a reversible tubal contraceptive device, in accordance with various embodiments of the subject technology.

Referring now to FIG. 18, the apparatus 10 may have tapered middle portion 22 and the flow reducing member 14 covering the frame 76. Alternatively, only one end (e.g., the distal portion 24) may be flared or widened as compared to the other (e.g., the middle portion 22 and proximal portion 20), still allowing for anchoring without pressure along the length of the apparatus 10. As illustrated, the flow reducing member 14 is external to the frame 76. However, the flow reducing member 14 may alternatively or additionally be internal or aligned with the frame 76, as generally described herein. The frame 76 may have a larger diameter when in an expanded mode than the flow reducing member 14. The flow reducing member 14 may be a collapsible outer element and the frame 76 may be an expandable inner element. The flow reducing member 14 and the frame 76 may be shaped, for example, with memory shape materials. In one or more embodiments, the flow reducing member 14 may be 10-16 mm long with a 1 mm outer diameter along its length, expandable by force up to about 7-8 mm. A distal end of the flow reducing member 14 may be extended outside of the frame 76 and reach its original low profile shape closing the distal end of the apparatus 10. The frame 76 may be about 10-16 mm long with a 2-3 mm outer diameter in the middle part, and 5-7 mm at both ends for better support and anchoring of the frame 76 in a biological tubal structure. In other words, the two metallic elements are communicating after deployment with two sets of forces acting in opposite directions.

The flow reducing member 14 may be coupled to the frame 76 such that when the frame 76 is positioned within the lumen of the reproductive structure (e.g., a fallopian tube 84), the flow reducing member 14 substantially impedes, reduces, or totally obstructs passage of sperm therethrough. The flow reducing member 14 may be formed of an impermeable or impenetrable material, or other materials described herein or otherwise useful for blockage and/or reduction in activity of sperm. The flow reducing member 14 may be formed of a single sheet or may be formed of multiple components, including the occlusion cap 86. The occlusion cap 86 may be provided as a component of the flow reducing member 14, or may be a separate component used with or without the flow reducing member 14. The occlusion cap 86 may be oriented substantially orthogonal to an axis of the lumen of the reproductive structure, providing a barrier with a minimal surface area. Moreover, the occlusion cap 86 may have a substantially flat surface, or may be curved or rounded, as illustrated. When curved, such curvature may be concave or convex, relative to the center of the apparatus 10. The occlusion cap 86 serves to occlude passage of sperm, and may be constructed of solid elastomeric polymer that does not allow tissue in-growth therethrough.

The occlusion cap 86 may be positioned on one or either of proximal portion 20 or the distal portion 24 and attached to or between metallic or otherwise rigid structures of the flow reducing member 14 and/or the frame 76. In one embodiment, the occlusion cap 86 may be positioned in the middle portion 22 or elsewhere in or on the apparatus 10. In some embodiments, multiple occlusion caps 86 may be positioned on or in the apparatus 10. For example, three occlusion caps 86 may be set in sequence from the distal portion 24 to the proximal portion 20 of the apparatus 10. In some embodiments, the flow reducing member 14 may have multiple occlusion caps 86 joined by an impermeable surface lying within the frame 76. In other embodiments, the impermeable surface of the flow reducing member 14 may lie partially or wholly outside the frame 76. In some embodiments, multiple frames 76 may be used with a single flow reducing member 14, and in other embodiments, multiple flow reducing members 14 may be used with a single frame 76. Similarly, in some embodiments, multiple apparatus 10 may be used in the same tubular structure, potentially providing a higher degree of blockage of the tubular structure.

The frame 76 may be constructed with a stronger material than that of the flow reducing member 14, thereby allowing the frame 76 to support the flow reducing member 14 and resist any tendency to collapse. Thus, the flow reducing member 14, including the occlusion cap(s) 86, may be presented as a sleeve resembling a sock or stockings placed or stretched over the stronger frame 76 shaped to support the flow reducing member 14. Both the frame 76 and the flow reducing member 14 may be fabricated from ribbon with rectangular shape. Both elements can be made from NiTi or medical grade steel, platinum or any other appropriate metal.

In one or more embodiments, the frame 76 may not be placed in direct contact with the inner wall 83 (FIG. 17) of the fallopian tube 84 or vas deferens (not shown), but may rather serve to support the flow reducing member 14 and the occlusion cap 86. Moreover, in some embodiments, it may be important for the frame 76 not to have direct contact with the biological structure, so as to reduce potential scar tissue growing over struts or structures of the frame 76.

For either or both of male and female contraception, the apparatus 10 may have physical properties that function to disable sperm from penetrating ovum. Such physical properties may include physically preventing sperm from passing through the apparatus 10 installed in the vas deferens and exiting the body of the male, physically preventing sperm from passing through the apparatus 10 installed in a fallopian tube 84 of a female's body and penetrating an ovum therein, or both. Additionally or alternatively, the flow reducing member 14 or other portion of the apparatus 10 may include an electrically-charged coating on the surface to "discharge" sperm, thereby reducing their energy and ability to penetrate into the fallopian tube 84. Such an electrically-charged barrier may be formed by ion coatings and may neutralize tail activity in sperm tails. Other coatings or spermacides may be used instead of or in conjunction with the electrically-charged coating. Such spermacides may be provided in the form of a renewable cartridge or other time released installation.

The flow reducing member 14 may be constructed of the bioabsorbable polymer or other materials indicated above, or metallic mesh. Thus, the coating may be removed from the surface of the flow reducing member 14, or otherwise made neutral so that the "discharging" or "disabling" effect to the sperm may be manipulated or otherwise terminated. In case of use of polymeric or metallic mesh, the size of mesh might be small enough to enable use of ionic charge of coating, but large enough to allow free sperm penetration upon removal of the charge. Similarly, the flow reducing member 14 may have an aperture large enough for passage of fluids but small enough to prevent passage of sperm. Alternatively, when the flow reducing member 14 provides multiple barriers, such as when two or more occlusion caps 86 are provided, an aperture may be formed in one of the barriers, but not all barriers, thereby allowing fluids to pass without providing a passageway for sperm.

When placing the apparatus 10 in the patient, the frame 76 may have an initially-shaped diameter larger than the flow reducing member 14, when both are deployed. Such diameter may be equal or about 1-2 mm larger than the biological tubular structure in which it is deployed. The flow reducing member 14 may be made with an initially-shaped diameter smaller than the tubular structure in which it is deployed and smaller than the outer diameter of the frame 76, thereby resulting in the flow reducing member 14 having a tendency to collapse when/if the frame 76 is removed therefrom. Delivery, visualization, and control methods may include endoscopic and angiography techniques.

Multiple apparatus 10 may be positioned in a single reproductive structure in sequence or simultaneously. Similarly, multiple apparatus 10 may be positioned in a patient to provide contraception. For example, in a female patient, each fallopian tube 84 may be provided with one or more apparatus 10. Likewise, in a male patient, each vas deferens may be provided with one or more apparatus 10. Thus, a method for prevention of sperm passage through a reproductive structure of a patient may involve positioning the elongate member 12 within a lumen (e.g., left fallopian tube 84) of the reproductive structure. The elongate member 12 may be arranged to form the frame 76, as described above. Once positioned in the lumen, the flow reducing member 14 coupled to the frame 76 may substantially impede, reduce, or totally obstruct passage of sperm through first lumen. The process may be repeated at another location within the same lumen, or may be repeated in another lumen (e.g., right fallopian tube 84), or both.

Figure 19:
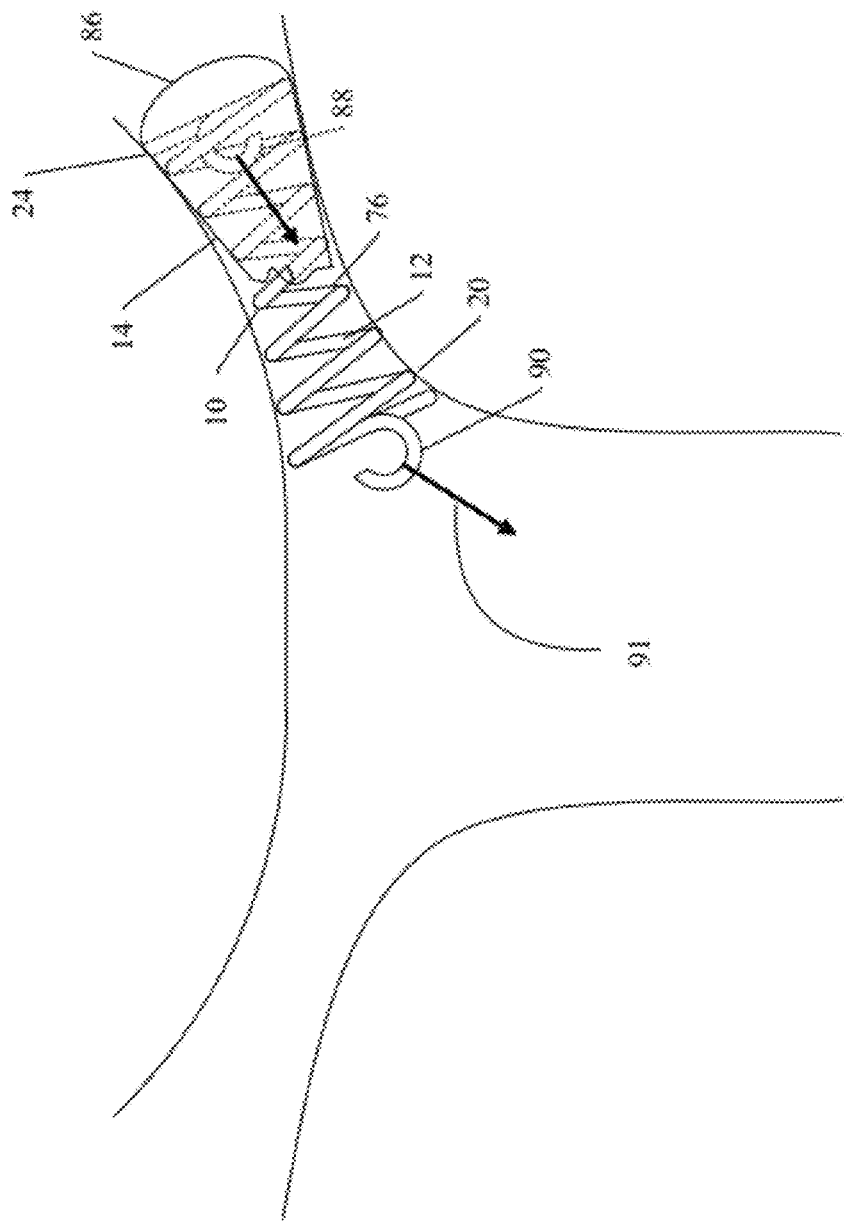
FIG. 19 illustrates removal of a reversible tubal contraceptive device, in accordance with various embodiments of the subject technology.

Referring to FIG. 19, removal of the apparatus 10 may involve use of a retrieving member (not shown) configured to engage or otherwise capture a withdrawal component, such as a first withdrawal component 88 associated with or otherwise coupled to the distal portion 24. As illustrated, the withdrawal component 88 is formed as a hook, but it will be appreciated that the withdrawal component 88 may be formed of various shapes or configurations without departing from the scope of the disclosure. In one or more embodiments, the first withdrawal component 88 may be made of polyethylene or nitinol, but may be made of other materials without departing from the scope of the disclosure.

The first withdrawal component 88 may be formed integrally with the distal portion 24 of the frame 76, or may be attached thereto using various means including, but not limited to, mechanical fasteners, welding techniques, adhesives, combinations thereof, or the like. In other embodiments, the first withdrawal component 88 may be an extension of the flow reducing member 14 or coupled thereto. In some embodiments, the first withdrawal component 88 may facilitate the retrieval of the elongate member 12 through inversion of the frame 76 or straightening of the frame 76 from its distal end. In operation, the retrieving member may pull the withdrawal component 88 proximally, toward an interior of the frame 76, thereby inverting the frame 76 and removing the apparatus 10.

Alternatively, removal may involve the use of a retrieving member engaging a second withdrawal component 90 associated with the proximal portion 20. Similar to the first withdrawal component 88, the second withdrawal component 90 may be formed integrally with the proximal portion 20 of the frame 76, or may be attached thereto using various means including, but not limited to, mechanical fasteners, welding techniques, adhesives, combinations thereof, or the like. Using the second withdrawal component 90, the apparatus 10 may be retrieved through tension to the frame 76 in the proximal direction 91, by pulling the withdrawal component 90 away from the interior of the frame 76. Thus, the frame 76 may be removed via a standard snare device or a specially-designed retriever, by pulling the frame 76 outward, causing the frame 76 to collapse from a coil-shaped structure into a straightened element, and allowing the flow reducing member 14 to collapse and be removed.

While complete removal of the apparatus 10 is one way to inactivate the apparatus 10 and restore fertility, the apparatus 10 may be inactivated in a number of other manners, as described herein. In instances where complete or even partial removal is undesirable, such as when scar tissue has formed over a portion of the apparatus 10, inactivation may be performed without surgical intervention. For example, fertility may be restored while the apparatus 10 remains in place by puncturing or otherwise compromising the integrity of flow reducing member 14 or the occlusion cap 86. As previously discussed, any of a variety of triggering events can cause material of the apparatus 10 to degrade rapidly, and thereby restore a passageway through the lumen. Thus, a method for restoring fertility to a patient having the apparatus 10 blocking sperm passage through a lumen of a reproductive structure may include deactivating the apparatus 10 in situ (i.e., at the delivery site of the apparatus 10 within the lumen). Such deactivating may include breaching the integrity of flow reducing member 14, and breaching may include any of puncturing, applying ultraviolet light, applying an electrical charge, applying a thermal charge, or otherwise triggering biodegradation.

Referring now to FIG. 20, illustrated is an exemplary application of the apparatus 10 used, for example, as a female contraceptive device, according to one or more embodiments of the disclosure. Specifically, a first apparatus 10a is shown deployed within a first (left) fallopian tube 84a, and a second apparatus 10b is shown deployed within a second (right) fallopian tube 84b. While in use, the apparatus 10a,b generally occlude the fallopian tubes 84a,b, respectively, and effectively sterilize the patient by preventing the passage of sperm or ovum therethrough. The apparatus 10a,b may be non-surgically implanted and subsequently inactivated or otherwise reversed non-surgically in order to restore fertility to the patient. Moreover, the apparatus 10a,b may be biocompatible to avoid eliciting a toxic response from the patient.

FIG. 21 illustrates an enlarged view of an exemplary apparatus 10, according to embodiments disclosed herein. As with prior embodiments, the apparatus 10 may be formed by a plurality of axially-spaced contiguous coils 34 extending between the proximal end 20 and the distal end 24. In some embodiments, the frame 76 is made of shape-memory materials, such as, but not limited to, nitinol. The frame 76 provides a generally cylindrical scaffolding or support structure over which the flow reducing member 14 can be arranged. In some embodiments, the flow reducing member 14 covers the frame 76 so as to generally close one end of the frame 76, such as the distal end 24, and define or otherwise define an opening 21 at the opposing end (i.e., the proximal end 20).

In one or more embodiments, the generally cylindrical shape of the frame 76 may be achieved by braiding wire (e.g., nitinol wire) or over a mandrel or other shape-forming device. The braided wire may be "heat set" by maintaining the wire in the desired shape while simultaneously exposing it to elevated temperatures. In some embodiments, between 8 strands and 48 strands of wire may be utilized to form the frame 76. In other embodiments, however, the frame 76 may be formed utilizing less than 8 strands or more than 48 strands, without departing from the scope of the disclosure, and depending at least partially on the desired dimensions of the application. In some embodiments, the wire used to form the frame 76 may have a diameter ranging between about 0.001 inches and about 0.010 inches. In other embodiments, however, the wire may have a diameter less than 0.001 inches and greater than 0.010 inches, without departing from the scope of the disclosure. The wires may be braided over a mandrel having an outside diameter that can range between about 0.080 inches and about 0.500 inches. Once properly heat set, the wire braid can be removed from the mandrel and altered, if desired, by compressing or elongating certain segments to achieve a more variable shape before being held constant to the new shape and exposed to a second round of heat setting.

In other embodiments, the cylindrical shape of the frame 76 may be achieved using a ribbon, such as nitinol ribbon, that is braided or otherwise wrapped around a mandrel or the like and subsequently heat set to the desired shape. In one or more embodiments, the ribbon may have a width ranging between about 0.2 mm and about 2 mm, and a thickness ranging between about 0.05 mm and 1 mm. As will be appreciated, the width and thickness of the exemplary ribbon may be varied to more or less without departing from the scope of the disclosure, and depending at least partially on the dimensions of the specific application. mandrel may have an outside diameter ranging between 9 mm and about 16 mm. In at least one embodiment, the ribbon may include a helix on one end of the frame 76 which reduces the outside diameter of the frame 76 at the distal end 24, for example, to about 0.1 mm to about 3 mm, seemingly closing the distal end 24 of the frame 76.

In yet other embodiments, the general shape of the frame 76 may be achieved by laser processing a sheet of shape-memory material, such as nitinol, to obtain a sheet thickness ranging between about 0.05 mm and about 1 mm. The sheet may then be heat set using, for example, a mandrel to form a generally cylindrical shape having an outside diameter that ranges between about 9 mm and about 16 mm. In at least one embodiment, the heat setting process reduces the outside diameter of the frame 76 at one end (e.g., the distal end 24) to between about 0.1 mm to about 3 mm, seemingly closing the distal end 24 of the frame 76. In yet other embodiments, the frame 76 may be made from shape-memory tubing, such as nitinol tubing, with segments removed by laser processing. After being laser processed, the tubing may be heat set in order to achieve an expanded outer diameter ranging between about 9 mm and about 16 mm diameter, with a reduced diameter at one end (e.g., the distal end 24) to between about 0.1 mm to about 3 mm, seemingly closing the distal end 24 of the frame 76.

The flow reducing member 14 may be an injection molded component that forms a thin-walled membrane configured to be positioned over the frame 76 so as to generally close one end (e.g., the distal end 24) of the apparatus 10. In some embodiments, the flow reducing member 14 covers the entire outer radial surface of the frame 76. In other embodiments, however, the flow reducing member 14 only covers a portion of the frame 76, such as described above with reference to FIG. 1. As shown in FIG. 21, the flow reducing member entirely encases the frame 76 except for an opening 21 defined at the proximal end 20 of the frame 76.

In some embodiments, the flow reducing member 14 is formed as a separate or individual component from the frame 76 and secured to the frame 76 by various means such as, but not limited to, adhesives, mechanical fixtures, combinations thereof, or the like. With the flow reducing member 14 coupled thereto, the frame 76 may be capable of maintaining an expanded outer diameter (e.g., 9 mm or larger). In other embodiments, however, the flow reducing member 14 may be manufactured as an integral part of the frame 76, thereby being integrated into the elastomeric matrix of the frame 76.

As generally described above, the flow reducing member 14 may be made from materials such as, but not limited to, silicone, polyurethane, polyethylene, fluoropolymers such as polytetrafluoroethylene, and bioabsorbable polymers. In at least one embodiment, the flow reducing member 14 is made of a silicone material having a durometer ranging between 00 A and about 50 A, and an elongation percentage of about 500% to about 1200%. In some embodiments, the silicone material may be dip cast or molded directly onto the outer radial surface of the frame 76. The silicone material may be cast or molded so as to obtain a wall thickness ranging between about 0.10 mm to about 1.00 mm. Those skilled in the art will appreciate that the durometer, elongation percentages, and wall thickness may vary, depending on the application, and nonetheless remain within the scope of the disclosure.

In some embodiments, the flow reducing member 14 is an absorbable polymer, such as a bioabsorbable polymer. As described above, the absorbable polymer may be a temporary occlusion device that reverses the fallopian tube 84 occlusion after a predetermined amount of time or after being exposed to a particular stimulus. This includes polymers which begin degradation by hydrolysis when positioned in the fallopian tube 84 or polymers which commence or accelerate degradation when the local environment is deliberately altered. Environmental changes include, but are not limited to, modification of local pH, modification of local temperature, and/or exposing the absorbable polymer to any of the following: ultrasound energy, irradiation, light, a solvent, an enzyme, fluids, a magnetic field, electricity, combinations thereof, or the like. In at least one embodiment, the absorbable polymer may be configured to remain intact or otherwise not fully degrade for a minimum of two years.

In one or more embodiments, the outer surface of the flow reducing member 14 may be coated with a lubricative substance, chemical, or material, thereby forming a lubricious coating. The lubricious coating may be configured to lubricate the outer surface of the flow reducing member 14, thereby making it less prone to tissue attachment and/or less prone to bonding to other surfaces. In one embodiment, the lubricious coating may be a chemical vapor deposited poly (p-xylylene) polymer, better known as Parylene. In one or more embodiments, Parylene C, AF-4, SF, and/or HT may be used, without departing from the scope of the disclosure. The chemical vapor deposition may have an applied thickness ranging between about 0.1 nm and about 1,000 nm, but may vary depending on the application. Using Parylene provides several advantages, such as its barrier properties, its cost, its use as an accepted coating for stents, defibrillators, pacemakers, and other devices permanently implanted into the body, and its other processing advantages. Moreover, Parylene C bonds well to silicone and can act as a barrier layer to occlude the nanoporous silica, prevent tissue in-growth, prevent bonding to other surfaces, and otherwise reduce the elastomeric surface friction coefficient.

Still referring to FIG. 21, the apparatus 10 further includes a withdrawal component 95. The withdrawal component 95 may serve substantially the same purpose as the first and second withdrawal components 88, 90 described above with reference to FIG. 19, that is, to facilitate the retrieval of the apparatus 10, or portions thereof, from the lumen of a patient's body. In some embodiments, the withdrawal component 95 is made of materials such as, but not limited to, polyethylene, nitinol, combinations thereof, or the like. Although relatively inert, polyethylene has been credited with triggering a white cell response capable of killing foreign sperm, which may prove advantageous for a contraceptive device application.

As illustrated, the withdrawal component 95 may be an elongate rod having a first end 96a and a second end 96b. The withdrawal component 95 may be configured to extend through the interior of the frame 76 and be either coupled to the frame 76 or the flow reducing member 14, or both, using various means including, but not limited to, mechanical fasteners, welding techniques, adhesives, combinations thereof, or the like. In at least one embodiment, the second end 96b of the withdrawal component 95 penetrates the distal end 24 of the frame 24 and/or the flow reducing member 14. In one embodiment, the withdrawal component 95 is an extension of the flow reducing member 14 and formed integrally therewith as a single component. In other embodiments, however, the withdrawal component 95 is an extension of the frame 76 and formed integrally therewith as a single component.

The first end 96a of the withdrawal component 95 may facilitate grasping of the withdrawal component 95 by a standard snare device or a specially-designed retriever (not shown). For example, the first end 96a may be formed as a hook, a ring, a textured surface, or the like, but it will be appreciated that the first end 96a may be formed of a variety of shapes and/or configurations suitable to facilitate grasping of the withdrawal component 95, without departing from the scope of the disclosure.

Removal of the apparatus 10, may be undertaken as generally described above. For example, in one embodiment the apparatus 10 may be removed by inverting the frame 76 within itself. This may be accomplished by pulling the withdrawal component 95 in the proximal direction, as indicated by the arrow 91. The withdrawal component 95 pulls the frame 76 proximally and toward its interior, thereby inverting the frame 76, as shown in FIG. 22. Once the frame 76 has been inverted, the apparatus 10 may be further advanced in the proximal direction 90 to fully remove the apparatus 10 from the patient. In other embodiments, however, only the frame 76 is removed using the withdrawal component 95, thereby leaving the flow reducing member 14 deployed within the fallopian tube 84 (FIG. 20).

Referring now to FIGS. 23, 24, and 25, illustrated are various stages of deploying and retrieving the apparatus 10, according to one or more embodiments disclosed. In FIG. 23, the apparatus 10 is positioned within a delivery device 98, such as a catheter as described above. Specifically, the frame 76 and the flow reducing member 14 are compressed within the delivery device 98, and the withdrawal device 95 extends concentrically therethrough. In the compressed configuration, the frame 76 biases against an inner surface 19 of the flow reducing member which is thereby forced into engagement with an inner surface 23 of the delivery device 98. For purpose of clarity, the flow reducing member 14 is not shown in FIG. 23 in direct contact with the inner surface 23 of the delivery device 98, but it will be appreciated that contact would nonetheless be made. In at least one embodiment, the delivery device 98 has an inner diameter of about 3 mm or less.

Once reaching the proper location within the fallopian tube 84 (FIG. 20), the delivery device 98 may be translated proximally such that the distal end 24 of the frame 76 and the second end 96b of the withdrawal device 85 extend past the opening 98a defined by the delivery device 98. In other embodiments, the delivery device 98 is maintained stationary and the apparatus 10 is moved distally in order to expose the distal end 24 of the frame 76 and the second end 96b of the withdrawal device 85 beyond the opening 98a.

As shown in FIG. 24, as the distal end 24 of the frame 76 exits the opening 98a and is no longer restrained by the delivery device 98, it begins to expand into its deployed configuration. As the frame 76 expands, the flow reducing member 14 expands simultaneously and is biased against an inner surface 84a (FIG. 25) of a fallopian tube 84 or other tubular structure of interest. As the remaining portions of the frame 76 and the flow reducing member 14 eventually exit the delivery device 98, the entire apparatus 10 becomes fully deployed within the fallopian tube 84. As an example, FIG. 21 shows the apparatus 10 in a fully-deployed configuration.

FIG. 25 illustrates an exemplary embodiment of the apparatus 10 as it is being removed from a fallopian tube 84, or other tubular structure, according to one or more embodiments. For simplicity or purposes of clarity, the frame 76 is not illustrated in FIG. 25. As generally described above, the apparatus 10 may be removed by inverting the frame 76 within itself, which may be accomplished by pulling the withdrawal component 95 in the proximal direction 91. As the flow reducing member 14 is pulled proximally, it detaches from the inner surface 84a of the fallopian tube 84 (or other tubular structure) and is eventually fully detached for removal.

Referring now to FIGS. 26 and 27, illustrated are alternative configurations of the apparatus 10, according to one or more embodiments. In order to better seat the apparatus 10 in varying-shaped tubular structures, and thereby achieve a better seal against the inner surface of said tubular structure, the frame 76 and/or the flow reducing member 14 may be formed or otherwise designed with varying circumferential profiles. For example, the apparatus 10 shown in FIG. 26 depicts a proximally-directed bell shape. Specifically, the frame 76 and/or the flow reducing member 14 may be formed to exhibit a generally bell-shaped structure, where the proximal end 20 of the frame 76 flares radially-outward. The embodiment shown in FIG. 26 may prove useful in seating the apparatus 10 in, for example, the opening of a fallopian tube 84, where the opening to the fallopian tube 84 is enlarged and also tapers outward in the proximal direction as it communicates with the uterus.

FIG. 27 reverses the configuration of the apparatus 10, and the withdrawing device 95 is instead coupled at or adjacent the proximal end 20 of the frame 76, thereby providing a distally-directed bell shape. In this configuration, the frame 76 is positioned with a distally-directed opening 21 that faces away from the uterus. Although a bell-shaped circumferential profile is shown in FIGS. 26 and 27, it will be appreciated that any number of circumferential profiles may be used, without departing from the scope of the disclosure, to fit any number of varying applications and varying shapes of tubular structures.

Referring now to FIG. 28, illustrated is another exemplary application of the apparatus 10 as used as a female contraceptive device, according to one or more embodiments disclosed. Specifically, the apparatus 10 may further include a tubular scaffold 99 configured to be positioned within the fallopian tube 84 (FIG. 20) and otherwise engage the inner surface 84a (FIG. 25) thereof. Accordingly, the tubular scaffold 99 may be configured to interpose the flow reducing member 14 (and/or the frame 76) and the inner surface 84a (FIG. 25) of the fallopian tube 84. The tubular scaffold 99 may be formed to exhibit a variety of cross-sectional shapes. For example, the tubular scaffold 99 can have a cross-sectional shape that is circular, elliptical, polygonal (e.g., triangular, rectangular, hexagonal, octagonal, etc.), combinations thereof, or the like. It will be appreciated by those skilled in the art that the tubular scaffolding 99, as generally described and illustrated herein, may be used in conjunction with any or all of the disclosed configurations of the apparatus 10, without departing from the scope of the disclosure.

In its deployed configuration, the frame 76 biases the flow reducing member 14 against an inner surface 100 of the tubular scaffold 99. In other embodiments, however, such as where the flow reducing device 14 is disposed within the interior of the frame 76 (see FIGS. 2 and 3), it is the frame 76 that biases against the inner surface 100 of the tubular scaffold 99. In operation, the tubular scaffold 99 shields the flow reducing member 14 and/or the frame 76 from the fallopian tube 84 wall, thereby preventing tissue in-growth into the flow reducing member 14 and/or the frame 76. Moreover, the tubular scaffold 99 generally prevents bonding of the flow reducing member 14 and/or the frame 76 to other surfaces which would prevent nonsurgical reversal of the apparatus 10. In at least one embodiment, the tubular scaffold 99 may remain implanted in the fallopian tube 84 upon removal of the apparatus 10, thereby helping facilitate non-surgical fertility reversal.

In some embodiments, the tubular scaffold 99 is made of a shape memory frame and may be deployed within the fallopian tube 84, or another tubular structure, in a manner substantially similar to a self-expanding stent. The tubular scaffold 99 may be made from braided metallic wires, formed to a particular dimension using a mandrel or the like. Specifically, the tubular scaffold 99 may be made from between about 8 and about 48 strands of braided metallic wire each having a diameter that ranges from about 0.001 inches to about 0.010 inches. The wire strands may be braided over a mandrel, for example, having an outside diameter that can range from about 0.080 inches to about 0.500 inches. As will be appreciated, however, the number of wire strands and the above-noted diameters may vary as more or less than noted above, without departing from the application, and depending on specific application dimensions.

In some embodiments, the tubular scaffold 99 may be encased partially or entirely with a coating. For example, the coating may be made of silicone having a durometer between 00 A and about 80 A, and an elongation percentage ranging between about 100% to about 1200%. The coating may be dip cast or injection molded directly onto the tubular scaffold 99 and may have a thickness that can range between about 0.10 mm to about 1.00 mm. In at least one embodiment, the coating applied to the tubular scaffold 99 may subsequently be coated with a lubricious substance or material, such as, for example, Parylene C. The lubricious coating may be applied, in one or more embodiments, to a thickness ranging from about 0.1 nm to about 1,000 nm.

Any or all of the exemplary apparatus 10 disclosed herein may further include the use of an occlusion gel as an additional barrier to more effectively prevent the passage of sperm and/or ovum. In at least one embodiment, the occlusion gel may be injected within or around the apparatus 10 using a catheter or other delivery device. The occlusion gel may add a radiopaque element to the apparatus 10, thereby providing increased radiopaque visibility to confirm proper placement of the apparatus 10. In addition to removing the apparatus 10, fertility may be restored by removing the occlusion gel. The occlusion gel may be removed, for example, by soft suction or the injection of saline with a temperature of less than about 37° C.

In some embodiments, the occlusion gel may be a precipitating gel. For example, the occlusion gel may be injected as a fluid which subsequently precipitates or otherwise converts into a gel-like substance in the presence of a stimulus, such as common physiological fluids. In at least one embodiment, this may require the concurrent injection of saline to help the occlusion gel precipitate sufficiently to fully occlude the fallopian tube 84. In other embodiments, the occlusion gel may be a phase transfer gel which is injected as a fluid and subsequently converts into a gel when exposed to elevated physiological temperatures. The phase transfer gel may dissolve when exposed to a reduced physiological temperature. Accordingly, the phase transfer gel may be removed by non-surgically injecting a lower temperature fluid, such as cold saline. In at least one embodiment, the phase transfer gel may further include barium sulfate, or a similar substance, to improve radiopaque visibility.

Moreover, any or all of the exemplary apparatus 10 disclosed herein may further include the use of an occlusion foam as an additional barrier to more effectively prevent the passage of sperm and/or ovum. The occlusion foam may be crimped and deployed or otherwise injected within or around the apparatus 10 using a catheter or other delivery device. At least one type of occlusion foam that may be used is a closed cell foam including a shape memory polymer having mean pore sizes ranging between about 1 micron to about 1,000 microns. Another type of occlusion foam that may be used is an open cell foam including a shape memory polymer having mean pore sizes of ranging between about 1 micron to about 500 microns. It will be appreciated, however, that many other types of occlusion foams may be utilized, without departing from the scope of the disclosure.

The occlusion foam may be configured to expand or enlarge when exposed to a fluidic environment and/or when exposed to elevated temperatures, thereby increasing the effective occlusion of the fallopian tube 84. In some embodiments, injection of the occlusion foam may require the concurrent injection of saline to aid in precipitation of the foam and thereby fully occlude the fallopian tube 84. In one or more embodiments, the occlusion foam may include a radiopaque element for better radiopaque visibility to confirm proper placement. To restore fertility, besides also removing the apparatus 10, the occlusion foam may be removed by soft suction through tubing, by mechanically grasping and withdrawing the resulting foam structure, or by capturing the resulting foam structure within the frame 76 as it is being removed proximally from the tubular structure.

In yet other embodiments, any or all of the exemplary apparatus 10 disclosed herein may further include the use of one or more types of particles disposed or otherwise arranged within the flow reducing membrane 14 in order to alter the environment and/or impede sperm activity/penetration. For example, polyglycolide particles may be arranged within (e.g., embedded, coated, etc.) the flow reducing membrane 14 and may serve to reduce the local pH, which has been shown to inhibit the movement of sperm.

The foregoing description is provided to enable a person skilled in the art to practice the various configurations described herein. While the present invention has been particularly described with reference to the various figures and configurations, it should be understood that these are for illustration purposes only and should not be taken as limiting the scope of the invention.

There may be many other ways to implement the invention. Various functions and elements described herein may be partitioned differently from those shown without departing from the scope of the invention. Various modifications to these configurations will be readily apparent to those skilled in the art, and generic principles defined herein may be applied to other configurations. Thus, many changes and modifications may be made to the invention, by one having ordinary skill in the art, without departing from the scope of the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. A method for preventing passage of sperm through a reproductive structure of a patient, comprising:
    positioning a first elongate member within a first lumen of the reproductive structure, the first elongate member comprising a first helical frame and a central longitudinal axis, the first helical frame comprising (i) a distal portion and a proximal portion, (ii) a shape-memory material expandable from a compressed configuration to a deployed configuration such that when unrestrained, the distal portion comprises a plurality of windings whose diameters are successively smaller in a distal direction, and (iii) a withdrawal component coupled to a smallest winding of the plurality of windings, and wherein in the deployed configuration, the withdrawal component extends at least partially along the central longitudinal axis proximally beyond the proximal portion;
    expanding the first helical frame within the first lumen;
    expanding a first flow reducing member coupled to the distal portion of the first helical frame, such that the first flow reducing member impedes passage of sperm through the first lumen with the first flow reducing member; and
    proximally retracting the withdrawal component to proximally invert the smallest winding through other windings of the plurality of windings such that the distal portion extends proximal to the proximal portion in an inverted configuration having a cross-sectional diameter smaller than a cross-sectional diameter of the proximal portion in the deployed configuration to permit removal of the first helical frame.

2. The method of claim 1, further comprising positioning a tubular scaffold in the first lumen to separate the first lumen from the first flow reducing member and the first helical frame.

3. The method of claim 1, further comprising injecting at least one of an occlusion gel and an occlusion foam within or around the first elongate member.

4. The method of claim 1, further comprising substantially covering the first distal portion with the first flow reducing member.

5. The method of claim 1, further comprising:
    positioning a second elongate member within a second lumen of the reproductive structure, the second elongate member forming a second helical frame and a second central longitudinal axis, the second helical frame comprising (i) a second distal portion and a second proximal portion; and (ii) a shape-memory material expandable from a compressed configuration to a deployed configuration such that when unrestrained, the second distal portion comprises a plurality of windings whose diameters are successively smaller in a distal direction, and (iii) a withdrawal component coupled to a smallest winding of the plurality of windings, and wherein in the deployed configuration, the withdrawal component extends at least partially along the central longitudinal axis proximally beyond the proximal portion;
    expanding the second helical frame within the second lumen;
    expanding a second flow reducing member coupled to the second helical frame, such that the second flow reducing member impedes passage of sperm through the second lumen with the second flow reducing member.

6. The method of claim 5, wherein the second helical frame further includes a second withdrawal component, coupled to the helical frame, and the method further comprises:
    engaging the second withdrawal component with a retrieving device; and
    pulling the second withdrawal component proximally to remove at least one of the second helical frame or the flow reducing member from the reproductive structure.

7. The method of claim 6, wherein the second withdrawal component is coupled to the second distal portion of the second helical frame, and pulling the second withdrawal component proximally further comprises pulling the second distal portion of the second helical frame toward an interior of the second helical frame, thereby inverting the second helical frame such that the second distal portion extends proximal to the second proximal portion in an inverted configuration to permit removal of the second helical frame member.

8. The method of claim 5, further comprising:
    deactivating the second flow reducing member such that sperm is permitted to pass through the second lumen.

9. The method of claim 8, wherein deactivating the second flow reducing member comprises breaching the integrity of the second flow reducing member.

10. The method of claim 8, wherein the second flow reducing member is an absorbable polymer and deactivating the second flow reducing member comprises accelerating degradation of the absorbable polymer.

11. The method of claim 1, further comprising:
    deactivating the first flow reducing member such that sperm is permitted to pass through the first lumen.

12. The method of claim 11, wherein deactivating the flow reducing member comprises breaching the integrity of the flow reducing member.

13. The method of claim 11, wherein the flow reducing member is an absorbable polymer and deactivating the flow reducing member comprises accelerating degradation of the absorbable polymer.

14. The method of claim 1, wherein in the deployed configuration, the withdrawal component extends substantially coaxially relative to the central longitudinal axis.

15. A method for preventing passage of sperm through a reproductive structure of a patient, comprising:
    positioning an elongate member within a lumen of the reproductive structure, the elongate member comprising a helical frame and a central longitudinal axis, the helical frame comprising (i) a distal portion and a proximal portion, (ii) a shape-memory material expandable from a compressed configuration to a deployed configuration such that when unrestrained, the distal portion comprises a plurality of windings having different diameters, the plurality of windings comprising a distalmost winding, and (iii) a withdrawal component being coupled to and intersecting a central section of the distalmost winding such that in the deployed configuration, the withdrawal component intersects the central longitudinal axis;
    expanding the helical frame within the lumen;
    expanding a flow reducing member coupled to the distal portion of the helical frame, such that the flow reducing member impedes passage of sperm through the lumen with the flow reducing member; and proximally retracting the withdrawal component to proximally invert the distalmost winding through other windings of the plurality of windings such that the distal portion extends proximal to the proximal portion in an inverted configuration having a cross-sectional diameter smaller than a cross-sectional diameter of the proximal portion in the deployed configuration to permit removal of the helical frame.

16. The method of claim 15, wherein the helical frame comprises a middle portion between the distal portion and the proximal portion, the middle portion having a cross-sectional diameter smaller than diameters of the distal and proximal portions.

17. The method of claim 16, wherein diameters of the plurality of windings the distal portion are successively larger in a distal direction.

18. The method of claim 15, wherein diameters of the plurality of windings of the distal portion are successively smaller in a distal direction.

19. The method of claim 15, wherein the helical frame further comprises a second withdrawal component coupled to the proximal portion, the method further comprising proximally retracting the second withdrawal component to facilitate removal of the helical frame from the lumen.

20. The method of claim 15, wherein in the deployed configuration, the withdrawal component extends substantially coaxially relative to the central longitudinal axis.

21. The method of claim 15, wherein the withdrawal component comprises a hook.

22. The method of claim 15, further comprising deactivating the flow reducing member such that sperm is permitted to pass through the lumen.

23. The method of claim 22, wherein deactivating the flow reducing member comprises breaching the integrity of the flow reducing member.

* * * * *